United States Patent
Tygesen et al.

(10) Patent No.: US 9,044,402 B2
(45) Date of Patent: **\*Jun. 2, 2015**

(54) ABUSE-DETERRENT PHARMACEUTICAL COMPOSITIONS FOR CONTROLLED RELEASE

(71) Applicant: Egalet Ltd., London (GB)

(72) Inventors: Peter Holm Tygesen, Vaerlose (DK); Karsten Lindhardt, Haslev (DK); Martin Rex Olsen, Holbaek (DK); Gina Engslev Fischer, Vaerlose (DK); Jan Martin Overgard, Frederikssund (DK); Georg Boye, Hedehusene (DK); Nikolaj Skak, Virum (DK); Torben Elhauge, Copenhagen K (DK)

(73) Assignee: EGALET LTD., London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/249,965

(22) Filed: Apr. 10, 2014

(65) Prior Publication Data

US 2014/0220126 A1    Aug. 7, 2014

Related U.S. Application Data

(63) Continuation of application No. 13/933,053, filed on Jul. 1, 2013.

(60) Provisional application No. 61/668,741, filed on Jul. 6, 2012.

(30) Foreign Application Priority Data

Jul. 6, 2012 (DK) .................................. 2012 70405

(51) Int. Cl.
*A61K 31/485* (2006.01)
*A61K 31/46* (2006.01)
*A61K 9/20* (2006.01)
*A61K 45/06* (2006.01)
*A61K 9/14* (2006.01)

(52) U.S. Cl.
CPC ............... *A61K 9/2031* (2013.01); *A61K 31/46* (2013.01); *A61K 45/06* (2013.01); *A61K 31/485* (2013.01); *A61K 9/146* (2013.01)

(58) Field of Classification Search
None
See application file for complete search history.

(56) References Cited

U.S. PATENT DOCUMENTS

| | | | |
|---|---|---|---|
| 2,685,553 A | 8/1954 | Carroll et al. | |
| 3,835,221 A | 9/1974 | Fulberth et al. | |
| 3,957,523 A | 5/1976 | Ohno et al. | |
| 4,034,758 A | 7/1977 | Theeuwes | |
| 4,330,338 A | 5/1982 | Banker | |
| 4,389,393 A | 6/1983 | Schor et al. | |
| 4,449,983 A | 5/1984 | Cortese et al. | |
| 4,503,067 A | 3/1985 | Wiedemann et al. | |
| 4,824,675 A | 4/1989 | Wong et al. | |
| 4,844,984 A | 7/1989 | Eckenhoff et al. | |
| 4,873,080 A | 10/1989 | Brickl et al. | |
| 4,892,742 A | 1/1990 | Shah | |
| 4,898,733 A | 2/1990 | De Prince et al. | |
| 5,019,396 A | 5/1991 | Ayer et al. | |
| 5,068,112 A | 11/1991 | Samejima et al. | |
| 5,102,668 A | 4/1992 | Eichel et al. | |
| 5,213,808 A | 5/1993 | Bar-Shalom et al. | |
| 5,266,331 A | 11/1993 | Oshlack et al. | |
| 5,352,455 A | 10/1994 | Robertson | |
| 5,411,745 A | 5/1995 | Oshlack et al. | |
| 5,419,917 A | 5/1995 | Chen et al. | |
| 5,422,123 A | 6/1995 | Conte et al. | |
| 5,460,826 A | 10/1995 | Merrill et al. | |
| 5,478,577 A | 12/1995 | Sackler et al. | |
| 5,508,042 A | 4/1996 | Oshlack et al. | |
| 5,520,931 A | 5/1996 | Persson et al. | |
| 5,549,912 A | 8/1996 | Oshlack et al. | |
| 5,593,695 A | 1/1997 | Merrill et al. | |
| 5,609,885 A | 3/1997 | Rivera et al. | |
| 5,614,218 A | 3/1997 | Olsson et al. | |
| 5,618,560 A | 4/1997 | Bar Shalom et al. | |
| 5,656,291 A | 8/1997 | Olsson et al. | |
| 5,656,295 A | 8/1997 | Oshlack et al. | |
| 5,667,805 A | 9/1997 | Merrill et al. | |
| 5,741,524 A | 4/1998 | Staniforth et al. | |
| 5,866,161 A | 2/1999 | Childers et al. | |
| 5,866,164 A | 2/1999 | Kuczynski et al. | |
| 5,869,097 A | 2/1999 | Wong et al. | |
| 5,879,705 A | 3/1999 | Heafield et al. | |
| 5,948,787 A | 9/1999 | Merrill et al. | |
| 5,952,005 A | 9/1999 | Olsson et al. | |

(Continued)

FOREIGN PATENT DOCUMENTS

| | | |
|---|---|---|
| DE | 102 23 844 A1 | 12/2003 |
| DE | 20 2006 014 131 U1 | 2/2007 |
| DE | 10 2006 057 364 A1 | 6/2008 |
| EP | 0 435 726 A2 | 7/1991 |
| EP | 0 493 513 A1 | 7/1992 |

(Continued)

OTHER PUBLICATIONS

Vippagunta et al. "Crystalline Solids," Advanced Drug Delivery Reviews, 2001, 48, pp. 18.*

(Continued)

*Primary Examiner* — Misook Yu
*Assistant Examiner* — Kauser M Akhoon
(74) *Attorney, Agent, or Firm* — Foley & Lardner LLP

(57) ABSTRACT

The present disclosure relates to pharmaceutical compositions that are abuse resistant and may also provide controlled release. The present disclosure also relates to the use of pharmaceutical compositions in the treatment of pain.

23 Claims, 20 Drawing Sheets

(56) References Cited

U.S. PATENT DOCUMENTS

| | | | |
|---|---|---|---|
| 5,968,551 | A | 10/1999 | Oshlack et al. |
| 6,066,339 | A | 5/2000 | Stark et al. |
| 6,077,533 | A | 6/2000 | Oshlack et al. |
| 6,077,538 | A | 6/2000 | Merrill et al. |
| 6,103,261 | A | 8/2000 | Chasin et al. |
| 6,143,328 | A | 11/2000 | Heafield et al. |
| 6,183,778 | B1 | 2/2001 | Conte et al. |
| 6,225,343 | B1 | 5/2001 | Behl et al. |
| 6,245,351 | B1 | 6/2001 | Nara et al. |
| 6,245,357 | B1 | 6/2001 | Edgren et al. |
| 6,267,981 | B1 | 7/2001 | Okamoto et al. |
| 6,267,985 | B1 | 7/2001 | Chen et al. |
| 6,277,384 | B1 | 8/2001 | Kaiko et al. |
| 6,284,274 | B1 | 9/2001 | Merrill et al. |
| 6,294,195 | B1 | 9/2001 | Oshlack et al. |
| 6,348,216 | B1 | 2/2002 | Kushla et al. |
| 6,375,957 | B1 | 4/2002 | Kaiko et al. |
| 6,383,471 | B1 | 5/2002 | Chen et al. |
| 6,395,299 | B1 | 5/2002 | Babich et al. |
| 6,399,096 | B1 | 6/2002 | Miller et al. |
| 6,451,848 | B1 | 9/2002 | Behl et al. |
| 6,458,824 | B1 | 10/2002 | Iwata et al. |
| 6,475,494 | B2 | 11/2002 | Kaiko et al. |
| 6,482,437 | B2 | 11/2002 | Debregeas et al. |
| 6,488,962 | B1 | 12/2002 | Berner et al. |
| 6,491,945 | B1 | 12/2002 | Childers et al. |
| 6,517,866 | B1 | 2/2003 | Am Ende et al. |
| 6,534,085 | B1 | 3/2003 | Zeligs |
| 6,562,375 | B1 | 5/2003 | Sako et al. |
| 6,572,885 | B2 | 6/2003 | Oshlack et al. |
| 6,599,531 | B2 | 7/2003 | Kushla et al. |
| 6,607,751 | B1 | 8/2003 | Odidi et al. |
| 6,632,832 | B1 | 10/2003 | Burman et al. |
| 6,696,066 | B2 | 2/2004 | Kaiko et al. |
| 6,709,678 | B2 | 3/2004 | Gruber |
| 6,730,326 | B2 | 5/2004 | Beyer et al. |
| 6,733,783 | B2 | 5/2004 | Oshlack et al. |
| 6,787,156 | B1 | 9/2004 | Bar-Shalom |
| 6,800,668 | B1 | 10/2004 | Odidi et al. |
| 7,060,293 | B1 | 6/2006 | Oshlack et al. |
| 7,063,864 | B1 | 6/2006 | Marechal et al. |
| 7,090,867 | B2 | 8/2006 | Odidi et al. |
| 7,144,587 | B2 | 12/2006 | Oshlack et al. |
| 7,172,767 | B2 | 2/2007 | Kaiko et al. |
| 7,201,920 | B2 | 4/2007 | Kumar et al. |
| 7,214,315 | B2 | 5/2007 | Shumway |
| 7,270,831 | B2 | 9/2007 | Oshlack et al. |
| 7,332,182 | B2 | 2/2008 | Sackler |
| 7,419,686 | B2 | 9/2008 | Kaiko et al. |
| 7,476,402 | B2 | 1/2009 | Kumar et al. |
| 7,510,726 | B2 | 3/2009 | Kumar et al. |
| 7,510,727 | B2 | 3/2009 | Oshlack et al. |
| 7,514,100 | B2 | 4/2009 | Oshlack et al. |
| 7,666,337 | B2 | 2/2010 | Yang et al. |
| 7,749,542 | B2 | 7/2010 | Kaiko et al. |
| 7,771,707 | B2 | 8/2010 | Hirsh et al. |
| 7,842,307 | B2 | 11/2010 | Oshlack et al. |
| 7,846,476 | B2 | 12/2010 | Oshlack et al. |
| 7,883,722 | B2 | 2/2011 | Bar-Shalom |
| 7,897,080 | B2 | 3/2011 | Yang et al. |
| 7,906,143 | B1 | 3/2011 | Odidi et al. |
| 7,943,174 | B2 | 5/2011 | Oshlack et al. |
| 7,981,439 | B2 | 7/2011 | Kumar et al. |
| 8,017,148 | B2 | 9/2011 | Sackler |
| 8,017,150 | B2 | 9/2011 | Yang et al. |
| 8,029,822 | B2 | 10/2011 | Faour et al. |
| 8,075,872 | B2 | 12/2011 | Arkenau-Maric et al. |
| 8,101,630 | B2 | 1/2012 | Kumar et al. |
| 8,105,631 | B2 | 1/2012 | Kaiko et al. |
| 8,114,383 | B2 | 2/2012 | Bartholomäus et al. |
| 8,114,384 | B2 | 2/2012 | Arkenau et al. |
| 8,133,507 | B2 | 3/2012 | Yum et al. |
| 8,142,811 | B2 | 3/2012 | Oshlack et al. |
| 8,147,870 | B2 | 4/2012 | Yum et al. |
| 8,153,152 | B2 | 4/2012 | Yum et al. |
| 8,168,217 | B2 | 5/2012 | Yum et al. |
| 8,173,152 | B2 | 5/2012 | Crowley et al. |
| 8,182,836 | B2 | 5/2012 | Mehta |
| 8,192,722 | B2 | 6/2012 | Arkenau-Maric et al. |
| 8,231,898 | B2 | 7/2012 | Oshlack et al. |
| 8,309,060 | B2 | 11/2012 | Bartholomaus et al. |
| 8,323,889 | B2 | 12/2012 | Arkenau-Maric et al. |
| 8,329,720 | B1 | 12/2012 | King et al. |
| 8,337,888 | B2 | 12/2012 | Wright et al. |
| 8,338,444 | B1 | 12/2012 | King et al. |
| 8,354,124 | B2 | 1/2013 | Yum et al. |
| 8,361,499 | B2 | 1/2013 | Oshlack et al. |
| 8,367,693 | B1 | 2/2013 | King et al. |
| 8,372,432 | B2 | 2/2013 | Han et al. |
| 8,377,453 | B2 | 2/2013 | Han et al. |
| 8,383,152 | B2 | 2/2013 | Jans et al. |
| 8,389,007 | B2 | 3/2013 | Wright et al. |
| 8,394,408 | B2 | 3/2013 | Han et al. |
| 8,409,616 | B2 | 4/2013 | Kumar et al. |
| 8,415,401 | B2 | 4/2013 | Yum et al. |
| 8,420,056 | B2 | 4/2013 | Arkenau-Maric et al. |
| 8,420,120 | B2 | 4/2013 | Yum et al. |
| 8,425,933 | B2 | 4/2013 | Mehta |
| 8,445,018 | B2 | 5/2013 | Habib et al. |
| 8,449,909 | B2 | 5/2013 | Hirsh et al. |
| 8,449,914 | B2 | 5/2013 | Andersen et al. |
| 8,460,640 | B2 | 6/2013 | Vinson et al. |
| 8,465,776 | B2 | 6/2013 | Hoarau |
| 8,470,361 | B2 | 6/2013 | Pettersson |
| 8,476,291 | B1 | 7/2013 | King et al. |
| 8,486,448 | B2 | 7/2013 | Rahmouni et al. |
| 8,486,449 | B2 | 7/2013 | Rahmouni et al. |
| 8,491,935 | B2 | 7/2013 | Mehta et al. |
| 8,501,160 | B2 | 8/2013 | Cailly-Dufestel et al. |
| 8,506,998 | B2 | 8/2013 | Miller et al. |
| 8,524,275 | B2 | 9/2013 | Oshlack et al. |
| 8,524,277 | B2 | 9/2013 | Edgren et al. |
| 8,529,948 | B1 | 9/2013 | Wright et al. |
| 8,563,038 | B2 | 10/2013 | Andersen et al. |
| 8,603,526 | B2 | 12/2013 | Tygesen et al. |
| 8,609,143 | B2 | 12/2013 | Fischer et al. |
| 8,609,683 | B2 | 12/2013 | Wright et al. |
| 8,617,605 | B2 | 12/2013 | Fischer et al. |
| 8,637,540 | B2 | 1/2014 | Kumar et al. |
| 8,685,447 | B2 | 4/2014 | Rahmouni et al. |
| 8,808,745 | B2 | 8/2014 | Fischer et al. |
| 2001/0036959 | A1 | 11/2001 | Gabel et al. |
| 2001/0036960 | A1 | 11/2001 | Decker et al. |
| 2001/0053791 | A1 | 12/2001 | Babcock et al. |
| 2002/0054911 | A1 | 5/2002 | Oh |
| 2003/0035836 | A1 | 2/2003 | Shanghvi et al. |
| 2003/0068375 | A1 | 4/2003 | Wright et al. |
| 2003/0077320 | A1 | 4/2003 | Childers et al. |
| 2003/0118641 | A1 | 6/2003 | Maloney et al. |
| 2003/0133976 | A1 | 7/2003 | Pather et al. |
| 2003/0203055 | A1 | 10/2003 | Rao et al. |
| 2003/0224051 | A1 | 12/2003 | Fink et al. |
| 2004/0010000 | A1 | 1/2004 | Ayer et al. |
| 2004/0028733 | A1 | 2/2004 | Tracy et al. |
| 2004/0089605 | A1 | 5/2004 | Brandt et al. |
| 2004/0091529 | A1 | 5/2004 | Edgren et al. |
| 2004/0102476 | A1 | 5/2004 | Chan et al. |
| 2004/0151772 | A1 | 8/2004 | Andersen et al. |
| 2004/0202717 | A1 | 10/2004 | Mehta |
| 2004/0213849 | A1 | 10/2004 | Sowden et al. |
| 2004/0224020 | A1 | 11/2004 | Schoenhard |
| 2004/0234602 | A1 | 11/2004 | Fischer et al. |
| 2004/0253310 | A1 | 12/2004 | Fischer et al. |
| 2005/0019399 | A1 | 1/2005 | Fischer et al. |
| 2005/0019405 | A1 | 1/2005 | Bar-Shalom |
| 2005/0053655 | A1 | 3/2005 | Yang et al. |
| 2005/0074493 | A1 | 4/2005 | Mehta et al. |
| 2005/0089569 | A1 | 4/2005 | Bar-Shalom |
| 2005/0106249 | A1 | 5/2005 | Hwang et al. |
| 2005/0158382 | A1 | 7/2005 | Cruz et al. |
| 2005/0163837 | A1 | 7/2005 | Boehm et al. |
| 2005/0169992 | A1 | 8/2005 | Jao et al. |
| 2005/0236741 | A1 | 10/2005 | Arkenau et al. |
| 2006/0002860 | A1 | 1/2006 | Bartholomaus et al. |

(56) References Cited

U.S. PATENT DOCUMENTS

| | | |
|---|---|---|
| 2006/0039864 A1 | 2/2006 | Bartholomaus et al. |
| 2006/0110327 A1 | 5/2006 | Emigh et al. |
| 2006/0165790 A1 | 7/2006 | Walden et al. |
| 2006/0177380 A1 | 8/2006 | Emigh et al. |
| 2006/0177507 A1 | 8/2006 | Faour et al. |
| 2006/0193782 A1 | 8/2006 | Bartholomaus et al. |
| 2006/0193912 A1 | 8/2006 | Ketsela et al. |
| 2006/0193914 A1 | 8/2006 | Ashworth et al. |
| 2007/0003616 A1 | 1/2007 | Arkenau-Maric et al. |
| 2007/0003617 A1 | 1/2007 | Fischer et al. |
| 2007/0003620 A1 | 1/2007 | Marechal et al. |
| 2007/0004797 A1 | 1/2007 | Weyers et al. |
| 2007/0020331 A1 | 1/2007 | Gold et al. |
| 2007/0042044 A1 | 2/2007 | Fischer et al. |
| 2007/0048228 A1 | 3/2007 | Arkenau-Maric et al. |
| 2007/0065510 A1 | 3/2007 | Odidi et al. |
| 2007/0122455 A1 | 5/2007 | Myers et al. |
| 2007/0183980 A1 | 8/2007 | Arkenau-Maric et al. |
| 2007/0190142 A1 | 8/2007 | Breitenbach et al. |
| 2007/0224129 A1 | 9/2007 | Guimberteau et al. |
| 2007/0231268 A1 | 10/2007 | Emigh et al. |
| 2007/0264326 A1 | 11/2007 | Guimberteau et al. |
| 2007/0264346 A1 | 11/2007 | Guimberteau et al. |
| 2007/0281003 A1 | 12/2007 | Fuisz et al. |
| 2008/0026052 A1 | 1/2008 | Schoenhard |
| 2008/0044454 A1 | 2/2008 | Yang et al. |
| 2008/0063725 A1 | 3/2008 | Guimberteau et al. |
| 2008/0069891 A1 | 3/2008 | Habib et al. |
| 2008/0102121 A1 | 5/2008 | Devane et al. |
| 2008/0113025 A1 | 5/2008 | Devane et al. |
| 2008/0152595 A1 | 6/2008 | Emigh et al. |
| 2008/0166405 A1 | 7/2008 | Mehta |
| 2008/0166407 A1 | 7/2008 | Shalaby et al. |
| 2008/0234352 A1 | 9/2008 | Fischer et al. |
| 2008/0247959 A1 | 10/2008 | Bartholomaus et al. |
| 2008/0248110 A1 | 10/2008 | Pettersson et al. |
| 2008/0248113 A1 | 10/2008 | Bartholomaus et al. |
| 2008/0254124 A1 | 10/2008 | Bar-Shalom |
| 2008/0299199 A1 | 12/2008 | Bar-Shalom et al. |
| 2008/0311187 A1 | 12/2008 | Ashworth et al. |
| 2008/0311205 A1 | 12/2008 | Habib et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0022790 A1 | 1/2009 | Flath et al. |
| 2009/0022798 A1 | 1/2009 | Rosenberg et al. |
| 2009/0041838 A1 | 2/2009 | Guimberteau et al. |
| 2009/0081290 A1 | 3/2009 | McKenna et al. |
| 2009/0169631 A1 | 7/2009 | Zamloot et al. |
| 2009/0202634 A1 | 8/2009 | Jans et al. |
| 2009/0274759 A1 | 11/2009 | Bar-Shalom et al. |
| 2009/0298862 A1 | 12/2009 | Yum et al. |
| 2009/0317355 A1 | 12/2009 | Roth et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0203130 A1 | 8/2010 | Tygesen et al. |
| 2010/0204259 A1 | 8/2010 | Tygesen et al. |
| 2010/0239667 A1 | 9/2010 | Hemmingsen et al. |
| 2010/0266701 A1 | 10/2010 | Guimberteau et al. |
| 2010/0291205 A1 | 11/2010 | Downie et al. |
| 2011/0008424 A1 | 1/2011 | Chang et al. |
| 2011/0020451 A1 | 1/2011 | Bartholomäus et al. |
| 2011/0038930 A1 | 2/2011 | Barnscheid et al. |
| 2011/0077238 A1 | 3/2011 | Leech et al. |
| 2011/0104214 A1 | 5/2011 | Oshlack et al. |
| 2011/0136847 A1 | 6/2011 | Chan et al. |
| 2011/0142905 A1 | 6/2011 | Bar-Shalom et al. |
| 2011/0159100 A1 | 6/2011 | Andersen et al. |
| 2011/0165248 A1 | 7/2011 | Machonis |
| 2011/0195989 A1 | 8/2011 | Rudnic et al. |
| 2011/0200681 A1 | 8/2011 | Habib et al. |
| 2011/0200715 A1 | 8/2011 | Fuisz et al. |
| 2011/0229526 A1 | 9/2011 | Rosenberg et al. |
| 2011/0229533 A1 | 9/2011 | Edgren et al. |
| 2011/0287093 A1 | 11/2011 | Schoenhard |
| 2012/0009129 A1 | 1/2012 | Brzeczko |
| 2012/0059065 A1 | 3/2012 | Barnscheid et al. |
| 2012/0065220 A1 | 3/2012 | Barnscheid et al. |
| 2012/0135075 A1 | 5/2012 | Mohammad |
| 2012/0136021 A1 | 5/2012 | Barnscheid et al. |
| 2012/0164220 A1 | 6/2012 | Huang |
| 2012/0201761 A1 | 8/2012 | Sackler |
| 2012/0202838 A1 | 8/2012 | Ghosh et al. |
| 2012/0202839 A1 | 8/2012 | Emigh et al. |
| 2012/0214777 A1 | 8/2012 | Crowley et al. |
| 2012/0251637 A1 | 10/2012 | Bartholomäus et al. |
| 2012/0321674 A1 | 12/2012 | Vachon et al. |
| 2012/0321713 A1 | 12/2012 | Han et al. |
| 2012/0321716 A1 | 12/2012 | Vachon et al. |
| 2013/0005823 A1 | 1/2013 | Emigh et al. |
| 2013/0022646 A1 | 1/2013 | Rudnic et al. |
| 2013/0028970 A1 | 1/2013 | Schwier et al. |
| 2013/0028972 A1 | 1/2013 | Schwier et al. |
| 2013/0084333 A1 | 4/2013 | Dick et al. |
| 2013/0090349 A1 | 4/2013 | Geißler et al. |
| 2013/0122087 A1 | 5/2013 | Habib et al. |
| 2013/0122101 A1 | 5/2013 | Habib et al. |
| 2013/0129826 A1 | 5/2013 | Geißler et al. |
| 2013/0171075 A1 | 7/2013 | Arkenau-Maric et al. |
| 2013/0171257 A1 | 7/2013 | Kumar et al. |
| 2013/0195981 A1 | 8/2013 | Pettersson |
| 2013/0195982 A1 | 8/2013 | Pettersson |
| 2013/0209557 A1 | 8/2013 | Barnscheid |
| 2013/0209560 A1 | 8/2013 | Hamed et al. |
| 2013/0217716 A1 | 8/2013 | Wright et al. |
| 2013/0230596 A1 | 9/2013 | Mehta |
| 2013/0245055 A1 | 9/2013 | Wright et al. |
| 2013/0251759 A1 | 9/2013 | Jans et al. |
| 2013/0251796 A1 | 9/2013 | McKenna et al. |
| 2013/0251797 A1 | 9/2013 | McKenna et al. |
| 2013/0251798 A1 | 9/2013 | McKenna et al. |
| 2013/0251799 A1 | 9/2013 | McKenna et al. |
| 2013/0251800 A1 | 9/2013 | McKenna et al. |
| 2013/0251801 A1 | 9/2013 | McKenna et al. |
| 2013/0251802 A1 | 9/2013 | McKenna et al. |
| 2013/0259938 A1 | 10/2013 | McKenna et al. |
| 2013/0259939 A1 | 10/2013 | McKenna et al. |
| 2013/0259940 A1 | 10/2013 | McKenna et al. |
| 2013/0260015 A1 | 10/2013 | McKenna et al. |
| 2013/0261143 A1 | 10/2013 | Wright et al. |
| 2013/0281480 A1 | 10/2013 | Yum et al. |
| 2013/0287845 A1 | 10/2013 | Yum et al. |
| 2013/0287849 A1 | 10/2013 | Andersen et al. |
| 2013/0287850 A1 | 10/2013 | Andersen et al. |
| 2013/0295168 A1 | 11/2013 | Yum et al. |
| 2013/0303494 A1 | 11/2013 | Wright et al. |
| 2013/0317049 A1 | 11/2013 | Yum et al. |
| 2013/0317051 A1 | 11/2013 | Oshlack et al. |
| 2013/0320592 A1 | 12/2013 | Arkenau-Maric et al. |
| 2013/0337059 A1 | 12/2013 | Yum et al. |
| 2013/0337060 A1 | 12/2013 | Yum et al. |
| 2013/0344142 A1 | 12/2013 | Rahmouni et al. |
| 2013/0344143 A1 | 12/2013 | Rosenberg et al. |
| 2014/0010873 A1 | 1/2014 | Tygesen et al. |
| 2014/0030327 A1 | 1/2014 | McKenna et al. |
| 2014/0050787 A1 | 2/2014 | Tygesen et al. |
| 2014/0120164 A1 | 5/2014 | Fischer et al. |

FOREIGN PATENT DOCUMENTS

| | | |
|---|---|---|
| EP | 0 406 315 B1 | 11/1992 |
| EP | 0 908 181 | 4/1999 |
| EP | 1 027 888 | 8/2000 |
| EP | 0 335 560 | 1/2002 |
| EP | 1 213 014 A2 | 6/2002 |
| EP | 1 371 360 | 5/2005 |
| EP | 1 547 670 A1 | 6/2005 |
| GB | 1430684 | 3/1976 |
| GB | 2170104 | 7/1986 |
| GB | 2182559 | 5/1987 |
| JP | 60/255719 | 12/1985 |
| JP | 07/100191 | 4/1995 |

(56) References Cited

FOREIGN PATENT DOCUMENTS

| | | |
|---|---|---|
| WO | WO 86/04817 | 8/1986 |
| WO | 89/09066 A1 | 10/1989 |
| WO | WO-89/09066 A | 10/1989 |
| WO | WO 90/08536 | 8/1990 |
| WO | 91/04015 A1 | 4/1991 |
| WO | WO-91-04015 A | 4/1991 |
| WO | WO 92/09270 | 6/1992 |
| WO | 95/22962 A1 | 8/1995 |
| WO | 96/00066 A1 | 1/1996 |
| WO | 96/08253 A1 | 3/1996 |
| WO | 97/33566 A2 | 9/1997 |
| WO | 99/44591 A1 | 9/1999 |
| WO | WO-99/44591 A | 9/1999 |
| WO | 99/51208 A1 | 10/1999 |
| WO | 00/41704 A1 | 7/2000 |
| WO | WO 01/35958 | 5/2001 |
| WO | WO 01/51035 | 7/2001 |
| WO | WO 01/51036 | 7/2001 |
| WO | WO 01/74357 | 10/2001 |
| WO | 02/056861 A2 | 7/2002 |
| WO | WO 02/065834 | 8/2002 |
| WO | 02/087512 A2 | 11/2002 |
| WO | WO 02/092078 | 11/2002 |
| WO | 03/024426 A1 | 3/2003 |
| WO | 03/024429 A1 | 3/2003 |
| WO | 03/024430 A1 | 3/2003 |
| WO | 03/026613 A1 | 4/2003 |
| WO | WO 03/039521 | 5/2003 |
| WO | 03/075897 A1 | 9/2003 |
| WO | 03/082204 A2 | 10/2003 |
| WO | 03/092648 A1 | 11/2003 |
| WO | 03/101384 A2 | 12/2003 |
| WO | 2004/002447 A2 | 1/2004 |
| WO | 2004/041252 A1 | 5/2004 |
| WO | 2004/047839 A1 | 6/2004 |
| WO | 2004/054542 A2 | 7/2004 |
| WO | 2004/056337 A2 | 7/2004 |
| WO | 2004/084868 A1 | 10/2004 |
| WO | 2004/084869 A1 | 10/2004 |
| WO | 2004/091512 A2 | 10/2004 |
| WO | 2004/093819 A2 | 11/2004 |
| WO | 2004/093843 A1 | 11/2004 |
| WO | 2005/000310 A1 | 1/2005 |
| WO | WO 2005/007074 | 1/2005 |
| WO | 2005/016313 A1 | 2/2005 |
| WO | 2005/016314 A1 | 2/2005 |
| WO | WO 2005/027878 | 3/2005 |
| WO | 2005/034859 A2 | 4/2005 |
| WO | 2005/053587 A1 | 6/2005 |
| WO | 2005/063206 A1 | 7/2005 |
| WO | 2005/063214 A1 | 7/2005 |
| WO | 2005/102286 A1 | 11/2005 |
| WO | 2005/107713 A2 | 11/2005 |
| WO | 2006/002883 A1 | 1/2006 |
| WO | 2006/002884 A1 | 1/2006 |
| WO | 2006/002886 A1 | 1/2006 |
| WO | 2006/015682 A1 | 2/2006 |
| WO | 2006/026504 A2 | 3/2006 |
| WO | 2006/030402 A2 | 3/2006 |
| WO | 2006/031209 A1 | 3/2006 |
| WO | 2006/058249 A2 | 6/2006 |
| WO | 2006/088305 A1 | 8/2006 |
| WO | 2006/089843 A2 | 8/2006 |
| WO | 2006/103418 A1 | 10/2006 |
| WO | 2006/106344 A2 | 10/2006 |
| WO | 2006/128471 A2 | 12/2006 |
| WO | 2007/014061 A2 | 2/2007 |
| WO | 2007/030402 A2 | 3/2007 |
| WO | 2007/085024 A2 | 7/2007 |
| WO | 2007/106550 A2 | 9/2007 |
| WO | 2007/112285 A2 | 10/2007 |
| WO | 2007/112286 A2 | 10/2007 |
| WO | 2007/131357 A1 | 11/2007 |
| WO | 2007/133583 A2 | 11/2007 |
| WO | 2007/135193 A2 | 11/2007 |
| WO | 2007/150074 A2 | 12/2007 |
| WO | 2007/150075 A2 | 12/2007 |
| WO | 2008/023261 A1 | 2/2008 |
| WO | 2008/027442 A2 | 3/2008 |
| WO | 2008/028047 A2 | 3/2008 |
| WO | 2008/033523 A1 | 3/2008 |
| WO | 2008/068471 A1 | 6/2008 |
| WO | 2008/086804 A2 | 7/2008 |
| WO | 2008/100375 A2 | 8/2008 |
| WO | 2008/107149 A2 | 9/2008 |
| WO | 2008/148798 A2 | 12/2008 |
| WO | 2009/035474 A1 | 3/2009 |
| WO | 2009/075782 A1 | 6/2009 |
| WO | 2009/076236 A2 | 6/2009 |
| WO | 2009/076764 A1 | 6/2009 |
| WO | 2009/088414 A2 | 7/2009 |
| WO | 2009/092601 A1 | 7/2009 |
| WO | 2009/104838 A1 | 8/2009 |
| WO | 2009/114648 A1 | 9/2009 |
| WO | 2010/017821 A1 | 2/2010 |
| WO | 2010/022726 A1 | 3/2010 |
| WO | 2010/032128 A1 | 3/2010 |
| WO | 2010/066034 A1 | 6/2010 |
| WO | 2010/069050 A1 | 6/2010 |
| WO | 2010/083843 A1 | 7/2010 |
| WO | 2010/083894 A1 | 7/2010 |
| WO | 2010/088911 A1 | 8/2010 |
| WO | 2010/089132 A1 | 8/2010 |
| WO | 2010/140007 A2 | 12/2010 |
| WO | 2010/151741 A1 | 12/2010 |
| WO | 2011/009602 A1 | 1/2011 |
| WO | 2011/009603 A1 | 1/2011 |
| WO | 2011/009604 A1 | 1/2011 |
| WO | 2011/041414 A1 | 4/2011 |
| WO | 2011/068723 A1 | 6/2011 |
| WO | 2011/079248 A1 | 6/2011 |
| WO | 2011/106416 A2 | 9/2011 |
| WO | 2012/028317 A1 | 3/2012 |
| WO | 2012/028318 A1 | 3/2012 |
| WO | 2012/028319 A1 | 3/2012 |
| WO | 2012/040651 A2 | 3/2012 |
| WO | 2012/061779 A1 | 5/2012 |
| WO | 2012/076907 A2 | 6/2012 |
| WO | 2012/080833 A2 | 6/2012 |
| WO | 2012/085656 A2 | 6/2012 |
| WO | 2012/085657 A2 | 6/2012 |
| WO | 2012/112952 A1 | 8/2012 |
| WO | 2012/131463 A2 | 10/2012 |
| WO | 2013/017234 A1 | 2/2013 |
| WO | 2013/017242 A1 | 2/2013 |
| WO | 2013/038267 A1 | 3/2013 |
| WO | 2013/038268 A1 | 3/2013 |
| WO | 2013/050539 A2 | 4/2013 |
| WO | 2013/057570 A2 | 4/2013 |
| WO | 2013/072395 A1 | 5/2013 |
| WO | 2013/077851 A1 | 5/2013 |
| WO | 2013/084059 A1 | 6/2013 |

OTHER PUBLICATIONS

Braga et al.; Stuct. Bond. 2009, 132, 25-50.*
Muller et al, Inorganic Structural Chemistry, 1993, John Wiley & Sons, pp. 14-15.*
Brannan et al., (Geometry 2nd Edition. Cambridge University Press: NY; 2012 p. 78).
Camu et al., "Pharmacology of Systemic Analgesics," *Best Practice & Research Clinical Anesthesiology* 16(4):475-488, 2002.
Dahlstrom et al., "Patient-Controlled Analgesic Therapy, Part IV: Pharmacokinetics and Analgesic Plasma Concentrations of Morphine," *Clinical Pharmacokinetics* 7:266-279, 1982.
Fischer et al., "Nonmedical Use of Prescription Opioids: Furthering a Meaningful Research Agenda," *J. Pain.* 9(6):490-449, 2008.
Graves et al., "Relationship Between Plasma Morphine Concentrations and pharmacologic Effects in Postoperative Patients Using Patient-Controlled Analgesia," *Clinical Pharmacology* 4:41-47, 1985.
Haahr et al. (Poster—Drug Abuse Resistant, Controlled Release using Egalet Dosage Units. Proceedings of the 34th Annual Meeting Exposition of the Controlled Release Society Jul. 7-11, 2007).

(56) References Cited

OTHER PUBLICATIONS

Hemmingsen et al., "Drug Abuse Resistant, Controlled Release, Using Egalet Dosage Units" poster. Published Jun. 28, 2007.
Katikaneni et al. "Ethylcellulose Matrix controlled Release Tablets of a Water-Soluble Drug," *International Journal of Pharmaceutics*, 119-125, 1995.
Qui et al., "Design Core-Shelled Polymer Cylinder for Potential Programmable Drug Delivery," *Int. J. Pharm.* 219:151-160, 2001.
Meyer et al., "Awareness Topic: Mitigating the Risks of Ethanol Induced Dose Dumping from Oral Sustained/Controlled Release Dosage Forms," FDA's ACPS Meeting, Oct. 2005.
National Institute on Drug Abuse, Monitoring the Future, "National Results on Adolescent Drug Use—Overview of Key Findings 2009," http://www.monitoringthefuture.org/ (Originally Published in May 2010).
National Institute on Drug Abuse, Monitoring the Future, "National Results on Adolescent Drug Use—Overview of Key Findings 2008," http://www.samhsa.gov/ (Originally Published in May 2009).
National Institute on Drug Abuse, 2008 http://www.nida.nih.gov/drugpages/prescription.html (Last Accessed on Jul. 15, 2008).
Raehhal & Bohn, "Mu Opioid Receptor Regulation and Opiate Responsiveness," *The AAPS Journal* 7(3): Article 60, 2005.
(www.rxlist.com/miralax-drug.htm) as referenced Oct. 19, 2011.
Roberts et al. "Enterohepatic Circulation: Physiological, Pharmacokinetic and Clinical Implications," *Clin. Pharmacokinet.* 41(10):751-790, 2002.
Notification of Transmittal of the International Search Report and the Written Opinion of the International Searching Authority issued Jul. 8, 2008 in International Application No. PCT/DK2008/000016.
International Preliminary Report on Patentability issued Jul. 16, 2009 in corresponding International Application No. PCT/DK2008/000016.
Notification of Transmittal of the International Search Report and the Written Opinion of the International Searching Authority issued Apr. 21, 2010 in International Application No. PCT/EP2010/000728.
International Preliminary Report on Patentability issued Aug. 6, 2011 in corresponding International Application No. PCT/EP2010/000728.
Notification of Transmittal of the International Search Report and the Written Opinion of the International Searching Authority issued May 28, 2010 in International Application No. PCT/DK2010/000019.
International Preliminary Report on Patentability issued Aug. 6, 2011 in corresponding International Application No. PCT/DK2010/000019.
International Search Report and the Written Opinion of the International Searching Authority issued Jan. 28, 2009 in International Application No. PCT/EP2008/056910.
Notification of Transmittal of the International Search Report and the Written Opinion of the International Searching Authority issued Feb. 6, 2010 in International Application No. PCT/DK2010/050016.
International Preliminary Report on Patentability issued Apr. 12, 2011 in International Application No. PCT/DK2010/050016.
International Type Search Report issued Jun. 17, 2009 in International Application No. PCT/DK2009/000192.
Office Action issued Oct. 17, 2012 in U.S. Appl. No. 12/701,429.
Response to First Office Action filed Mar. 13, 2013 in U.S. Appl. No. 12/701,429.
Notice of Allowance issued Jul. 24, 2013 in U.S. Appl. No. 12/701,429.
Amendment after Notice of Allowance filed Aug. 26, 2013 in U.S. Appl. No. 12/701,429.
First Office Action issued Feb. 24, 2012 in U.S. Appl. No. 12/701,248.
Response to first Office Action filed Jun. 21, 2012 in U.S. Appl. No. 12/701,248.
Second Office Action issued Jul. 20, 2012 in U.S. Appl. No. 12/701,248.
Response to Jul. 20, 2012 Office Action filed Oct. 22, 2012 in U.S. Appl. No. 12/701,248.
Interview Summary issued Dec. 12, 2012 in U.S. Appl. No. 12/701,248.
Preliminary Amendment filed Jul. 13, 2009 in U.S. Appl. No. 12/523,045.
Office Action issued Oct. 26, 2011 in U.S. Appl. No. 12/523,045.
Response to Oct. 26, 2011 Office Action filed Feb. 21, 2012 in U.S. Appl. No. 12/523,045.
Office Action issued May 24, 2012 in U.S. Appl. No. 12/523,045.
Response to May 24, 2012 Office Action filed Aug. 7, 2012 in U.S. Appl. No. 12/523,045.
Interview Summary issued Dec. 14, 2012 in U.S. Appl. No. 12/523,045.
Supplemental Amendment filed Jul. 11, 2013 in U.S. Appl. No. 12/523,045.
First Office Action issued Mar. 7, 2013 in U.S. Appl. No. 12/602,953.
First Office Action issued Apr. 11, 2012 in U.S. Appl. No. 12/694,197.
Response to First Office Action filed Jul. 11, 2012 in U.S. Appl. No. 12/694,197.
Final Office Action issued Sep. 14, 2012 in U.S. Appl. No. 12/694,197.
Response to Final Office Action filed Mar. 13, 2013 in U.S. Appl. No. 12/694,197.
First Office Action issued Nov. 14, 2011 in U.S. Appl. No. 12/823,067.
Response to Nov. 14, 2011 Office Action filed May 14, 2012 in U.S. Appl. No. 12/823,067.
Final Office Action issued Sep. 10, 2012 in U.S. Appl. No. 12/823,067.
Interview Summary issued Dec. 20, 2012 in U.S. Appl. No. 12/823,067.
Response to Sep. 10, 2012 Final Office Action filed Jan. 10, 2013 in U.S. Appl. No. 12/823,067.
Notice of Allowance issued Jun. 11, 2013 in U.S. Appl. No. 12/823,067.
Bravo et al., "In-vitro studies of diclofenac sodium controlled-release from biopolymeric hydrophilic matrices," *J. Pharmaceutical Science*, vol. 5, No. 3, pp. 213-219 (2002).
The Condensed Chemical Dictionary, "mixture," 9th edition, p. 584 (1977).
Giunchedi et al., "Hydrophilic matrices for the extended release of a model drug exhibiting pH-dependent solubility," *International Journal of Pharmaceutics*, vol. 85, pp. 141-147 (1992).
Hoshi et al., Cellulose and its Derivatives, pp. 24-25 (1992).
Miyazaki et al., "In situ-gelling gellan formulations as vehicles for oral drug delivery," *J. Control Release*, vol. 60, pp. 287-295 (1999).
Rowe et al., "Glycerin," *Handbook of Pharmaceutical Excipients*, Pharmaceutical Presse, $4^{th}$ edition, pp. 257-258 (2003).
www.wikipedia.org, web page on phosphoric acid, http://en.wikipedia.org/wiki/Phosphoric_acid, May 8, 2007.
Yamakita et al., "In Vitro/in Vivo Evaluation of Two Series of TA5707F Controlled Release Matrix Tablets Prepared with Hydroxypropyl Methyl Cellulose Derivatives with Entero-Soluble or Gel-Formation Properties," *Biol. Pharm. Bull*, vol. 18, No. 10, pp. 1409-1416 (1995).
Office Action issued Oct. 24, 2006 by the Examiner in U.S. Appl. No. 10/703,084 (US 2004/0151772).
Office Action issued Jun. 14, 2007 by the Examiner in U.S. Appl. No. 10/703,084 (US 2004/0151772).
Office Action issued Dec. 20, 2007 by the Examiner in U.S. Appl. No. 10/827,521 (US 2005/0019405).
Office Action issued Jul. 25, 2006 by the Examiner in U.S. Appl. No. 10/490,308 (US 2004/0234602).
Office Action issued Mar. 9, 2007 by the Examiner in U.S. Appl. No. 10/490,308 (US 2004/0234602).
Office Action issued Oct. 3, 2006 by the Examiner in U.S. Appl. No. 10/490,170 (US 2005/0019399).
Office Action issued May 9, 2007 by the Examiner in U.S. Appl. No. 10/490,170 (US 2005/0019399).
Office Action issued May 14, 2008 by the Examiner in U.S. Appl. No. 10/845,522 (US 2005/0089569).
Office Action issued Jun. 16, 2006 by the Examiner in U.S. Appl. No. 10/845,522 (US 2005/0089569).

(56) References Cited

OTHER PUBLICATIONS

Office Action issued Oct. 27, 2005 by the Examiner in U.S. Appl. No. 10/845,522 (US 2005/0089569).
Office Action issued Jul. 29, 2005 by the Examiner in U.S. Appl. No. 10/845,522 (US 2005/0089569).
Office Action issued Mar. 21, 2007 by the Examiner in U.S. Appl. No. 10/845,522 (US 2005/0089569).
Office Action issued Dec. 23, 2008 by the Examiner in U.S. Appl. No. 10/550,685 (US 2007/0042044).
Office Action issued Dec. 15, 2008 by the Examiner in U.S. Appl. No. 12/213,087 (US 2008/0254124).
Office Action issued Jun. 16, 2009 by the Examiner in U.S. Appl. No. 10/550,453 (US 2007/0042044).
Office Action issued Jan. 13, 2009 by the Examiner in U.S. Appl. No. 10/845,522 (US 2005/0089569).
Office Action issued Jun. 17, 2009 by the Examiner in U.S. Appl. No. 10/550,685 (US 2007/0042044).
Office Action issued Apr. 29, 2009 by the Examiner in U.S. Appl. No. 12/076,105 (US 8,449,914).
Office Action issued Sep. 29, 2009 by the Examiner in U.S. Appl. No. 12/076,105 (US 8,449,914).
Office Action issued Apr. 5, 2010 by the Examiner in U.S. Appl. No. 12/076,105 (US 8,449,914).
Office Action issued Nov. 10, 2009 by the Examiner in U.S. Appl. No. 10/550,453 (US 2007/0003617).
Office Action issued Apr. 13, 2010 by the Examiner in U.S. Appl. No. 10/550,453 (US 2007/0003617).
Office Action issued Mar. 1, 2010 by the Examiner in U.S. Appl. No. 10/550,685 (US 2007/0042044).
Office Action issued Nov. 4, 2009 by the Examiner in U.S. Appl. No. 10/845,522 (US 2005/0089569).
Office Action issued Oct. 6, 2010 by the Examiner in U.S. Appl. No. 10/845,522 (US 2005/0089569).
Office Action issued on Jun. 18, 2010 by the Examiner in U.S. Appl. No. 12/076,105 (US 8,449,914)).
Office Action issued Aug. 3, 2006, in U.S. Appl. No. 10/490,169, 11 sheets.
Office Action issued Mar. 2, 2007, in U.S. Appl. No. 10/490,169, 13 sheets.
Office Action issued on Apr. 24, 2012 in U.S. Appl. No. 12/076,105 (US 8,449,914).
Office Action issued on Jan. 20, 2011 in U.S. Appl. No. 10/550,453 (US 2007/0003617).
Office Action issued on Jun. 7, 2011 in U.S. Appl. No. 10/550,453 (US 2007/0003617).
Office Action issued on Aug. 5, 2010 by the Examiner in U.S. Appl. No. 10/550,685 (US2007/0042044).
Final Office Action issued on Feb. 1, 2012 by the Examiner in U.S. Appl. No. 10/550,685 (US2007/0042044).
Notice of allowarice issued on Jun. 5, 2012 by the Examiner in U.S. Appl. No. 10/550,685 (US2007/0042044).
Office Action issued on Feb. 18, 2011 in U.S. Appl. No. 12/076,105 (US 8,449,914).
Notice of Allowance issued on Feb. 11, 2013 in U.S. Appl. No. 12/076,105 (US 8,449,914).
Office Action issued on Mar. 31, 2011 in U.S. Appl. No. 12/073,692 (US 8,449,914).
Office Action issued on Dec. 6, 2012 in U.S. Appl. No. 12/073,692 (US 8,449,914).
Office Action issued on Oct. 11, 2011 in U.S. Appl. No. 12/073,692 (US 2008/0254122).
Office Action issued on Jul. 10, 2012 in U.S. Appl. No. 12/073,692 (US 2008/0254122).
Office Action issued on Apr. 28, 2011 in U.S. Appl. No. 12/073,691 (US 2008/0254122).
Office Action issued on Jun. 9, 2011 in U.S. Appl. No. 12/073,691 (US 2008/0254122).
Office Action issued on Oct. 27, 2011 in U.S. Appl. No. 12/073,691 (US 2008/0254122).
Office Action issued on Jan. 31, 2012 in U.S. Appl. No. 12/642,416 (US 2010/0166866).
Office Action issued on Dec. 13, 2011 in U.S. Appl. No. 11/915,655 (US 2009/0274759).
Office Action issued on Jun. 20, 2012 in U.S. Appl. No. 11/915,655 (US 2009/0274759).
Wikipedia, "Phosphoric Acid," http://en.wikipedia.org/wiki/Phosphoric_acid downloaded May 10, 2012.
Wanka et al., "Phase Diagrams and Aggregation Behavior of Poly(oxyethylene)-Poly(oxyethelene) Tribolock Copolymers in Aqueous Solutions," Macromolecules, vol. 27, pp. 4145-4159, 1994.
Packer et al., "Molecular Aspects of a-Tocotrienol Antioxidant Action and Cell Signaling," Journal of Nutrition, vol. 131, No. 2, pp. 369S-373S, 2001.
Marvola et al., "Enteric polymers as binders and coating materials in multiple-unit site-specific drug delivery systems," *European Journal of Pharmaceutical Sciences*, vol. 7, pp. 259-267, 1999.
Dubbs et al., "Solubility of Vitamin E ($\alpha$-Tocopherol) and Vitamin $K_3$ (Menadione) in Ethanol-Water Mixture," *J. Chem. Eng. Data*, vol. 43, pp. 590-591, 1998.
Merck Index ($9^{th}$ ed.) Entry No. 9681 for Vitamin E, p. 1290, 1976.
Varshosaz et al., "Use of enteric polymers for production of microspheres by extrusion-spheronization," *Pharmaceutica Acta Helvetiae*, vol. 72, pp. 145-152. 1997.
Kais Group, "Hydrogentated Palm Kernel Oil," http://kaisgroup.us/our-products/palm-oil-products/hydrogentated-palm-kernel-oil. Published 2011.
Soy Info Center, "A Special Report on the History of Soy Oil, Soybean Meal & Modern Soy Protein Products," http://soyinfocenter.com/HSS/hydrogenation2.php, published 2007.
Polysciences, Inc., "Monomers & Polymers," http://www.polysciences.com/Catalog/Department/Product/98/categoryid-298/productid--422/, published Apr. 3, 2004.
Notice of Allowance issued on Jul. 3, 2014 in U.S. Appl. No. 10/550,453 (US2007/0003617).
Office Action issued on Mar. 18, 2014 in U.S. Appl. No. 10/550,453 (US 2007/0003617).
Office Action issued on Feb. 6, 2014 in U.S. Appl. No. 13/974,689 (US 2014/0120164).
Office Action issued on Jun. 10, 2014 in U.S. Appl. No. 13/933,053 (US 2014/0010873).
Office Action issued on Jan. 28, 2014 in U.S. Appl. No. 13/974,346 (US 8,808,745).
Notice of Allowance issued on Jun. 19, 2014 in U.S. Appl. No. 13/974,346 (US 8,808,745).
Office Action issued on Jan. 20, 2015 in U.S. Appl. No. 13/933,053 (US 2014/0010873).
Notice of Allowance issued on Jan. 20, 2015 in U.S. Appl. No. 13/928,135 (US 2013/0287849).
Notice of Allowance issued Jan. 23, 2015 in U.S. Appl. No. 12/701,248 (US 2010/0204259).
Office Action issued on Feb. 25, 2015 in U.S. Appl. No. 13/974,689 (US 2014/0120164).
Office Action issued on Mar. 6, 2015 in U.S. Appl. No. 14/331,833 (US 2015/0037417).

* cited by examiner

| Fractiles | | |
|---|---|---|
| 10% fractile | 156 | μm |
| 25% fractile | 201 | μm |
| 50% fractile | 274 | μm |
| 75% fractile | 425 | μm |
| 90% fractile | 1547 | μm |

| Fractiles | | |
|---|---|---|
| 10% fractile | 121 | µm |
| 25% fractile | 165 | µm |
| 50% fractile | 244 | µm |
| 75% fractile | 424 | µm |
| 90% fractile | 1114 | µm |

| Fractiles | | |
|---|---|---|
| 10% fractile | 197 | μm |
| 25% fractile | 242 | μm |
| 50% fractile | 332 | μm |
| 75% fractile | 497 | μm |
| 90% fractile | 721 | μm |

ABUSE-DETERRENT PHARMACEUTICAL COMPOSITIONS FOR CONTROLLED RELEASE

RELATED APPLICATIONS

This application is a continuation of U.S. application Ser. No. 13/933,053, filed Jul. 1, 2013, which claims the benefit under 35 U.S.C. 119(e) of U.S. Provisional Application No. 61/668,741, filed on Jul. 6, 2012, the contents of which are incorporated herein by reference.

All patent and non-patent references cited in the application are hereby incorporated by reference in their entirety.

FIELD OF INVENTION

The present disclosure relates to pharmaceutical compositions. In certain embodiments, the pharmaceutical compositions according to the present description are abuse-deterrent and may provide controlled release.

BACKGROUND OF INVENTION

Increased attention has been drawn to the abuse of prescription pharmaceutical compositions. The abuse, or non-medicinal use, of prescription pharmaceutical compositions has been reported to be an increasing problem. In North America, abuse of prescription pharmaceutical compositions has become an important issue for the U.S. Food and Drug Administration (FDA), and the pharmaceutical industry is striving to develop abuse-deterrent pharmaceutical compositions in order to reduce the potential for misuse of prescription pharmaceutical compositions. Prescription pharmaceutical compositions that are typically misused fall, primarily, into three groups: 1) Opioids prescribed for pain; 2) Central Nervous System (CNS) depressants prescribed for anxiety or sleep problems; and 3) Stimulants, prescribed, for example, for attention deficit hyperactivity, narcolepsy, or obesity.

Methods for abusing prescription pharmaceutical compositions are varied and can include, for example, extraction, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, and administration as suppository. Alcohol-induced dose dumping of active drug substance from prescription pharmaceutical compositions also presents potential abuse and safety problems.

DETAILED DESCRIPTION OF THE INVENTION

Figure 1:
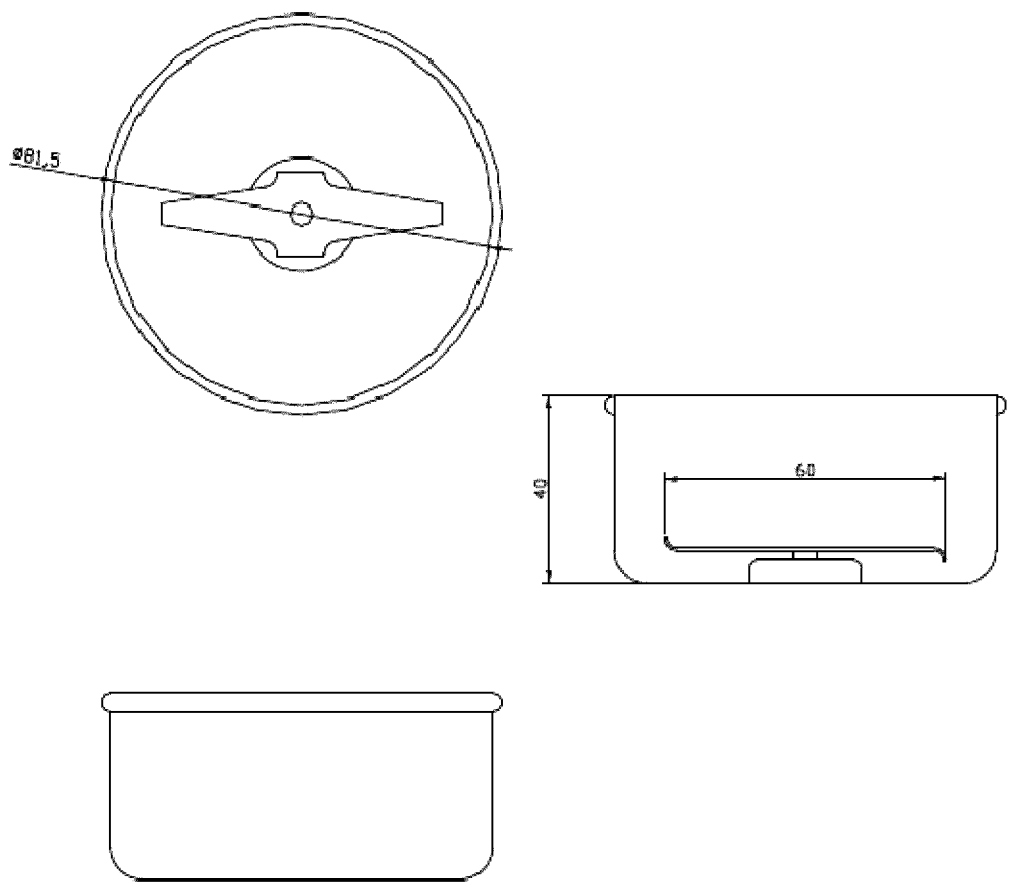
FIG. 1 shows a drawing of a Moulinex-1411R coffee grinder chamber with stainless steel blades.

The present disclosure provides novel abuse-deterrent pharmaceutical compositions, which are resistant to abuse and tampering. In certain embodiments, the pharmaceutical compositions according to the present description, even without containing an outer shell, exhibit hardness that is resistant to physical tampering. In particular embodiments, the pharmaceutical compositions disclosed herein may be formulated in such a way that the composition maintains a desired release profile of the active drug substance, even if the pharmaceutical composition is subjected to physical tampering.

One embodiment of the present disclosure provides an abuse-deterrent pharmaceutical composition, comprising: (a) an active drug substance; (b) a polyethylene oxide; and (c) optionally, a plasticizer, wherein the pharmaceutical composition does not provide immediate release of the active drug substance after physical tampering, and wherein when at least one polyethylene oxide has a molecular weight of at least 1,000,000 daltons, then the pharmaceutical composition comprises at least 5% w/w plasticizer.

In particular embodiments, the pharmaceutical compositions disclosed herein may comprise a controlled released abuse-deterrent pharmaceutical composition with a route of administration that may prevent or limit the feeling of euphoria combined with preventing or making it more difficult to abuse the active drug substance from the composition by, for example, injection, smoking, snorting, swallowing, sublingual or buccal administration, chewing, and administration as suppository.

The abuse-deterrent pharmaceutical compositions according to the present description can be further understood when studied relative to a comparator. Comparison of the abuse-deterrent pharmaceutical compositions disclosed herein to a comparator assesses the incremental and meaningful improvement in the ability of said pharmaceutical compositions to deter abuse or misuse.

In addition, certain embodiments of the present disclosure relate to the use of the disclosed pharmaceutical compositions in the treatment of a clinical condition (such as pain) in an individual in need thereof.

DEFINITIONS

For purposes of the present disclosure, "dose dumping" refers to an unintended, rapid release of the entire amount or a significant fraction of the active drug substance contained within a prescription pharmaceutical composition over a short or accelerated period of time. For purposes of abuse, alcohol-induced dose dumping may facilitate isolation or concentration of active drug substances from a prescription pharmaceutical composition. Alternatively, dose dumping in the presence of alcohol may increase the ease with which a prescription pharmaceutical composition can be abused simply through the intake of an alcoholic beverage concomitantly with the prescription pharmaceutical composition. Moreover, alcohol-induced dose dumping may present safety issues outside the context of abuse. For example, a patient taking a prescription pharmaceutical composition for medicinal purposes may inadvertently cause delivery of a dose of active drug substance that is too high or absorbed too quickly by self-administering a pharmaceutical composition shortly before, simultaneously with, or shortly after, consumption or intake of an alcoholic beverage or another pharmaceutical composition containing alcohol (e.g., an over-the-counter cold or flu medicine).

The term "physical tampering," as used herein, refers to any kind of physical interference or manipulation that may result in particle size reduction of a pharmaceutical composition. Hence, compositions that are resistant to physical tampering are formulated in such a way that the composition cannot readily be size reduced to a form that is suitable for abuse, such as, for example, injection or snorting, because the tablet cannot easily be ground, grated, dissolved, and the like. Examples of physical tampering include, but are not limited to, crushing, grinding, grating, cutting, crisping, and other methods of particle size reduction.

The term "controlled release," as used herein, denotes pharmaceutical composition that provide extended release of an active drug substance from the composition for an extended period of time. In certain circumstances, the term "controlled release" is used to designate a release at a desired rate during a predetermined release period. Additional or alternative terms, such as, for example, "modified", "delayed", "sustained", "prolonged", "extended" release may be used, in certain embodiments, as synonyms to the term "controlled release."

The term "immediate release," as used herein, denotes a pharmaceutical composition that releases the active drug substance (80% release) within at the most 30 minutes, when subjected to dissolution test according to USP 35, NF 30, (711), Apparatus 2.

Polyethylene Oxide

The pharmaceutical compositions of the present disclosure comprise a polyethylene oxide. Polyethylene oxides (PEOs) are linear polydisperse nonionic polymers composed of repeating units of ethylene oxide. Their chemical formula is $HO[CH_2CH_2O]_nH$, where n represents the average number of oxyethylene groups. See the structural presentation of polyethylene oxide below, wherein n is the average number of oxyethylene groups. Depending on preparation method, high molecular weight PEO may have one terminal methyl group.

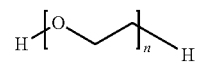

Polyethylene oxides that are suitable for use in the pharmaceutical compositions according to the present description are those having an average molecular weight of at least about 200,000 daltons, such as an average molecular weight of in the range of about 200,000 to about 10,000,000 daltons, for example in the range of about 250,000 to about 10,000,000 daltons, such as in the range of about 300,000 to about 10,000,000 daltons, for example in the range of about 350,000 to about 10,000,000 daltons, such as in the range of about 400,000 to about 10,000,000 daltons. In certain embodiments, the polyethylene oxides that are suitable for use in the compositions disclosed herein are those having an average molecular weight of at the most 1,000,000 daltons, such as an average molecular weight of in the range of about 200,000 to about 1,000,000 daltons, for example in the range of about 300,000 to about 1,000,000 daltons, such as in the range of about 400,000 to about 1,000,000 daltons. In another embodiment, the polyethylene oxides that are suitable for use in the compositions disclosed herein are those having an average molecular weight of at the most 500,000 daltons, such as an average molecular weight of in the range of about 200,000 to about 500,000 daltons, for example in the range of about 250,000 to about 500,000 daltons, such as in the range of about 300,000 to about 500,000 daltons, for example in the range of about 350,000 to about 500,000 daltons, such as in the range of about 400,000 to about 500,000 daltons. In yet another embodiment, the polyethylene oxides suitable for use in the compositions described herein are those having an average molecular weight of at the most 400,000 daltons, such as in the range of about 100,000 to about 400,000 daltons, for example in the range of about 200,000 to about 400,000 daltons, such as in the range of about 300,000 to 400,000 daltons. In one embodiment, the pharmaceutical composition comprises polyethylene oxides having an average molecular weight of 400,000 daltons.

In certain embodiments, the polyethylene oxides suitable for use in the compositions described herein are those having an average molecular weight selected from 200,000 daltons, 250,000 daltons, 300,000 daltons, 350,000 daltons, 400,000 daltons, 450,000 daltons, 500,000 daltons, 550,000 daltons, 600,000 daltons, 650,000 daltons, 700,000 daltons, 750,000 daltons, 800,000 daltons, 850,000 daltons, 900,000 daltons, 950,000 daltons, 1,000,000 daltons, 2,000,000 daltons, 3,000,000 daltons, 4,000,000 daltons, 5,000,000 daltons, 7,000,000 daltons, 10,000,000 daltons.

In certain embodiments, the total concentration of polyethylene oxide for use in the composition is in the range of 5 to 99.9% w/w, such as from 10 to 99.9% w/w, such as from 10 to 98% w/w, such as from 20 to 98% w/w, such as from 30 to 98% w/w, such as from 40 to 98% w/w, such as from 50 to 98% w/w, such as from 60 to 98% w/w, such as from 70 to 98% w/w, calculated as w/w % of the composition.

In particular embodiments, the level of polyethylene oxide 200,000 daltons to achieve the desired viscosity as described herein may be at least 1,020 mg, for polyethylene oxide 300,000 daltons it is at least 544 mg, for polyethylene oxide 400,000 daltons it is at least 435 mg, for polyethylene oxide 600,000 daltons it is at least 324 mg, for polyethylene oxide 900,000 daltons it is at least 243 mg, for polyethylene oxide 1,000,000 daltons it is at least 203 mg for polyethylene oxide 2,000,000 daltons and 4,000,000 daltons it is at least 162 mg and for polyethylene oxide 5,000,000 daltons, 7,000,000 daltons and 10,000,000 daltons it is at least 122 mg.

In some embodiments, the upper level of polyethylene oxide 200,000 to 10,000,000 daltons to achieve the desired viscosity in pharmaceutical compositions described herein is approximately 1,100 mg.

The compositions as described herein may comprise mixtures of polyethylene oxides with different average molecular weights, for example, in order to obtain polyethylene oxides with a desirable average molecular weight. Thus, in some embodiments, the pharmaceutical comprises different polyethylene oxide materials with different average molecular weights.

In certain embodiments, in order to obtain polyethylene oxide with a desirable average molecular weight, it is important to note that, in such cases, it is necessary to use polyethylene oxides, which have an average molecular weight closest to the desired molecular weight to ensure a narrow chain length distribution. In certain such embodiments, for example, equal amounts of polyethylene oxide 200,000 daltons and polyethylene oxide 600,000 daltons may be mixed to obtain polyethylene oxide 400,000 daltons.

A composition as described herein may comprise more than one different kind of polyethylene oxide, such as 2, for example 3, such as 4, for example 5, such as more than 5 different polyethylene oxides. In certain such embodiments, the composition comprises 1 to 4 different polyethylene oxides. In one such embodiment, the composition comprises 1 to 3 different polyethylene oxides. In another such embodiment, the composition comprises 2 different polyethylene oxides.

The polyethylene oxide used in compositions according to the present description may have a melting point higher than the body temperature of the individual (e.g., a human) in which the pharmaceutical composition is to be used. Thus, in particular embodiments, the polyethylene oxides employed in the pharmaceutical compositions described herein may have a melting point of in the range of 38° C. to 200° C., such as in the range of 38° C. to 150° C., for example in the range of 38° C. to 120° C., such as in the range of 38° C. to 100° C., for example in the range of 65° C. to 100° C.

Plasticizer

A composition as described herein may also comprise at least one plasticizer.

In particular embodiments, the composition comprises a poloxamer.

A composition as described herein may comprise more than one different kind of plasticizer, such as 2, for example 3, such as more than 3 different plasticizers. In certain such embodiments, the composition comprises 1 to 3 different plasticizers. In one such embodiment, the composition comprises 2 different plasticizers. In another such embodiment, the different kind of plasticizer is a different kind of poloxamer.

In one embodiment, the composition comprises one or more plasticizers, preferably one or more plasticizers selected from the group consisting of poloxamers, such as poloxamer 188 and/or poloxamer 407.

In some embodiments, the composition comprises at least one poloxamer. Poloxamers may be copolymers or block copolymers and are a range of non-ionic surfactants of polyethylene glycol (PEG) and polypropylene glycol (PPG).

The poloxamer may be Diol EO/PO block copolymers, which, for example, in chemical abstracts are described under the scientific name hydroxy-hydroxypoly(oxyethylene) poly(oxypropylene)-poly(oxyethylene)-block copolymer in combination with the CAS register number. In specific embodiments, a suitable poloxamer for use in a composition of the disclosure has a HLB value of at least about 18 such as, for example, at least approximately 20, preferably at least 24. In certain embodiments, the average molecular weight of a suitable poloxamer is typically at least about 2,000 daltons.

Block copolymers of ethylene oxide and propylene oxide that may be included in the composition described herein have a molecular weight of at least 2,000 daltons, typically in the range of 3,000 to 30,000 daltons, such as in the range of 4,000 to 15,000 daltons.

Exemplary poloxamers that may be used in the compositions disclosed herein have the formula $HO(C_2H_4O)_a(C_3H_6O)_b(C_2H_4O)_aH$, where "a" is an integer from 10 to 150, such as from 30 to 140, for example from 50 to 100, such as from 65 to 90, for example from 70 to 90, and "b" is an integer from 10 to 80, such as from 15 to 80, for example from 20 to 60, such as from 25 to 55.

Other plasticizers may be incorporated in the composition of the pharmaceutical compositions as described herein. A suitable plasticizer may be selected from mono- and di-acetylated monoglycerides, diacetylated monoglycerides, acetylated hydrogenated cottonseed glyceride, glyceryl cocoate, polyethylene glycols (for example with a molecular weight below 35,000 daltons) or polyethylene oxides (for example with a molecular weight of about 35,000 to 600,000 daltons), dipropylene glycol salicylate glycerin, fatty acids and esters, phthalate esters, phosphate esters, amides, diocyl phthalate, phthalyl glycolate, mineral oils, hydrogenated vegetable oils, vegetable oils, acetylated hydrogenated soybean oil glycerides, castor oil, acetyl tributyl citrate, acetyl triethyl citrate, methyl abietate, nitrobenzene, carbon disulfide, beta-naphtyl salicylate, sorbitol, sorbitol glyceryl tricitrate, fatty alcohols, cetostearyl alcohol, cetyl alcohol, stearyl alcohol, oleyl alcohol, myristyl alcohol, sucrose octaacetate, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2,000, polyoxyethylene 50 stearate, macrogol ethers, cetomacrogol 1000, lauromacrogols, nonoxinols, octocinols, tyloxapol, poloxamers, polyvinyl alcohols, polysorbate 20, polysorbate 40, polysorbate 60, polysorbate 65, polysorbate 80, polysorbate 85, sorbitan monolaurate, sorbitan monooleate, sorbitan monopalmitate, sorbitan monostearate, sorbitan sesquioleate, sorbitan trioleate, sorbitan tristearate and sucrose esters, amyl oleate, butyl oleate, butyl stearate, diethylene glycol monolaurate, glycerol tributyrate, Cumar W-1, Cumar MH-1, Cumar V-1, Flexol B-400, monomeric polyethylene ester, Piccolastic A-5, Piccalastic A-25, Beckolin, Clorafin 40, acetyl tributyl citrate, acetyl triethyl citrate, benzyl benzoate, butoxyethyl stearate, butyl and glycol esters of fatty acids, butyl diglycol carbonate, butyl ricinoleate, butyl phthalyl butyl glycolate, camphor, dibutyl sebacate, dibutyl tartrate, diphenyl oxide, glycerine, HB-40, hydrogenated methyl ester of rosin, methoxyethyl oleate, monoamylphthalate, Nevillac 10, Paracril 26, technical hydroabietyl alcohol, Methylene glycol dipelargonate, solid aliphatic alcohols, and mixtures thereof.

In particular embodiments, the composition comprises cetostearyl alcohol, castor oil, dibutyl sebacate, polyethylene oxides and/or poloxamer as plasticizer. In another embodiment, the composition comprises polyethylene glycols, cetostearyl alcohol, cetyl alcohol, stearyl alcohol, alfa-tocopheryl polyethylene glycol succinate (TPGS), tocopheryl derivative, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, poloxamers, polysorbate 40, polysorbate 60, polysorbate 65, polysorbate 80, polysorbate 85, acetyl tributyl citrate and/or acetyl triethyl citrate as plasticizer. However, in other embodiments, other plasticizers may also be used to provide desired material properties.

In certain embodiments, the amount of plasticizer in the composition is in the range of from 0 to 60% w/w, for example in the range of 0 to 50% w/w, such as in the range of 0 to 40% w/w, for example in the range of 0 to 30% w/w, such as in the range of 0 to 20% w/w. In some embodiments, the amount of plasticizer in the composition is at least 1% w/w, for example at least 5% w/w, such as for example at least 10% w/w. In some embodiments, the amount of plasticizer in the matrix composition is at the most 20% w/w, such as in the range of 0 to 20% w/w, for example 5 to 20% w/w, such as in the range of 10 to 20% w/w, for example 15 to 20% w/w. In other embodiments the amount of plasticizer in the matrix composition is at least 5% w/w, such as in the range of 5 to 25% w/w, for example 5 to 15% w/w, such as in the range of 5 to 10% w/w.

In some embodiments, the plasticizer is a poloxamer. In certain such embodiments, the amount of poloxamer in the composition is at the most 20% w/w, such as in the range of 0 to 20% w/w, for example 5 to 20% w/w, such as in the range of 10 to 20% w/w, for example 15 to 20% w/w. In other embodiments, the amount of poloxamer in the composition is at least 5% w/w, such as in the range of 5 to 25% w/w, for example 5 to 15% w/w, such as in the range of 5 to 10% w/w.

In particular such embodiments, the composition comprises one or more plasticizer(s) and one or more polymer(s).

Active Drug Substance

An active drug substance suitable for use in the pharmaceutical compositions described herein is a therapeutically, prophylactically and/or diagnostically active drug substance (herein also abbreviated as "active substance" or "active drug substance").

Examples of specific active drug substances suitable for use in the pharmaceutical compositions provided herein include:

Anti-inflammatory and antirheumatic active drug substances, such as, for example: butylpyrazolidines, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicams, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine and bucillamine;

Analgesics, such as, for example: opioids, natural opium alkaloids, morphine, opium, hydromorphone, nicomorphine, oxycodone, dihydrocodeine, diamorphine, tapentadol, papavereturn, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, ziconotide;

Anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocalne, butanilicaine, cinchocaine, etidocaine, articaine, ropivacaine, levobupivacaine, esters of benzoic acid, cocaine, other local anaesthetics, such as, for example: ethyl chloride, dyclonine, phenol, capsaicin;

Antimigraine active drug substances, such as, for example: ergot alkaloids, dihydroergotamine, ergotamine, methysergide, lisuride, corticosteroid derivatives, flumedroxone, selective serotonin (5HT1) agonists, sumatriptan, naratriptan, zolmitriptan, rizatriptan, almotriptan, eletriptan, frovatriptan, other antimigraine preparations, pizotifen, clonidine, iprazochrome, dimetotiazine, oxetorone;

Antiepileptic active drug substances, such as, for example: barbiturates and derivatives, methylphenobarbital, phenobarbital, primidone, barbexaclone, metharbital, hydantoin derivatives, ethotoin, phenyloin, amino(diphenylhydantoin) valeric acid, mephenyloin, fosphenyloin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, beclamide;

Anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, etybenzatropine;

Dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine oxidase B inhibitors, selegiline, rasagiline, other dopaminergic agents, such as, for example: tolcapone, entacapone, budipine;

Antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopenthixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, paliperidone;

Anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclo-octadiene derivatives, benzoctamine, azaspirodecanedione derivatives, buspirone, other anxiolytics, such as, for example: mephenoxalone, gedocarnil, etifoxine;

Hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, etallobarbital, allobarbital, proxibarbal, aldehydes and derivatives, chloral hydrate, chloralodol, acetylglycinamide chloral hydrate, dichloralphenazone, paraldehyde, benzodiazepineemepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, dipiperonylaminoethanol;

Antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, amineptine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lisdexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, vinpocetine;

Anti-dementia active drug subtances, such as, for example: anticholinesterases, tacrine, donepezil, rivastigmine, galantamine, other anti-dementia drugs, memantine, and *ginkgo biloba;*

Other nervous system active drug substances, such as, for example: parasympathomimetics, anticholinesterases, neostigmine, pyridostigmine, distigmine, ambenonium, choline esters, carbachol, bethanechol, other parasympathomimetics, such as, for example: pilocarpine, choline alfoscerate;

Active drug substances used in addictive disorders, such as, for example: nicotine, bupropion, varenicline, disulfuram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, amifampridine;

Opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodeine, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, dimethoxanate.

In certain embodiments, the active drug substance may, for example, be an active drug substance with abuse potential that presents a safety risk. Such active drug substance may, for example, be selected from:

1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine, 1-phenylcyclohexylamine, 1-piperidinocyclohexanecarbonitrile, 2,5-dimethoxy-4-ethylamphetamine, 2,5-dimethoxyamphetamine, 2C-B-(4-bromo-2,5-dimethoxypenethylamine), 2C-D (2,5-dimethoxy-4-methylphenethylamine), 2C-I (4-iodo-2,5-dimethoxy-phenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiopenethylamine), 3,4-methylenedioxymethamphetamine, 3,4,5-trimethoxyamphetamine, 3,4-methylenedioxyamphetamine, 3,4-methylenedioxy-N-ethylamphetamine, 3-methylfentanyl, 3-methylthiofentanyl, 4-bromo-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-diisopropyl-tryptamine), 5-MeO-DMT (5-methoxy-N,N-dimethyl-tryptamine), 5-methoxy-3,4-methylenedioxyamphetamine, acetorphin, acetorphine, acetyl-alpha-methylfentanyl, acetyl-alpha-methylfentanyl, acetyldihydrocodeine, acetylmethadol, acetylmethadol, alfentanil, allobarbital, allyprodin, allyprodine, alphacetylmethadol except levo-alphacetylmethadol, alpha-ethyltryptamine, aphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amylnitrit (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylketon, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamin, bromazepam, brotizolam, bufotenine, buprenorphine, butabarbital, butalbital, butobarbital, butorphanol, BZP (A 2) (1-benzylpiperazin), camazepam, cannabis, carfentanil, catha edulis, cathine, cathinone, chloral betaine, chloral hydrate, chlordiazepoxide, chlorhexadol, chlorotestosterone (same as clostebol), chlorphentermine, clobazam, clonazepam, clonitazene, clonitrazepate, clortermine, clostebol, clotiazepam, cloxazolam, coca leaves, cocaine, codeine, codeine & isoquinoline alkaloid, codeine methylbromide, codeine-N-oxide, codoxim, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodeine, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidin, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the sepcies psilocype semilanceata, furethidine, gammahydroxybutanic acid, glutethimide, halazepam, haloxazolam, heroine, hydrocodone, hydrocodone & isoquinoline alkaloid, hydromorphinol, hydromorphone, hydroxypethidine, ibogaine, isobutylnitrit, isomethadone, ketamine, ketazolam, ketobemidone, levamfetamine, levo-alphacetylmethadol, levo-methamphetamine, levomethorphan, levomoramide, levophenacylmorphan, levorphanol, lisdexamfetamin, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine), mCPP (1-(3-chlorphenyl)piperazine), mebutamate, mecloqualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandranone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrole, piritramide, PMMA (paramethyxymethyl amphetamine), prazepam, proheptazine, properidine, propiram, psilocybine, psilocyn, pyrovalerone, quazepam, pacemethorphane, racemoramide, racemorphane, remifentanil, salvia divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamin, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine & zolazepam in combination, tilidine, trenbolone, triazolam, trimeperidine, vinbarbital, zaleplon, zipeprol, zolpidem and zopiclon.

Other suitable examples of active drug substances suitable for use in the pharmaceutical compositions described herein include, for example, alfentanil, allylprodine, alphaprodine, aniloridine, benzylmorphine, bezitramide, buprenorphine, butophanol, clonitazene, codeine, cyclazocine, desomorphine, dextromoramide, dezocine, diapromide, dihydrocodeine, dihydromorphine, dimenoxadol, dimephetanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narccine, nicomorphine, norlevorphanol, normethadone, nalorphine, normorphine, norpipanone, opium, oxycodone, oxycodeine, oxymorphone, papavereturn, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanil, ohmefentanyl, MPPP, prodine, PEPAP, levomethorphan, etorphine, lefetamine, loperamide, diphenoxylate or pethidine.

Even further examples of active drug substances suitable for use in the pharmaceutical compositions described herein include anabolic steroids, cannabis, cocaine and diazepam.

In one embodiment, the active drug substance is selected from the group consisting of the therapeutic classes including non-steroidal anti-inflammatory substances and antirheumatic active drug substances.

In other embodiments, the active drug substance is selected from therapeutic classes including analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-andrenergic, serotonin, H3 antagonists used for ADHD and nootropics agents used in addictive disorders.

In still further embodiments, the active drug substance is selected from therapeutic classes including anaesthetics, centrally-acting analgesics, sedative-hypnotics, anxiolytics, appetite suppressants, decongestants, antitussives, antihistamines, antiemetics, antidiarrheals, and drugs used to treat narcolepsy and attention deficit hyperactivity disorder.

In certain embodiments, the active drug substance is associated with abuse syndromes and the active drug substance may, for example, be selected from opioids, CNS depressants, CNS stimulants, cannabinoids, nicotine-like compounds, glutamate antagonists and N-methyl-D-aspartate (NMDA) antagonists.

In specific embodiments, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodeine, diamorphine, tapentadol, papavereturn, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, ziconotide.

In certain such embodiments, the active drug substance is an opioid. Where an opioid is included as an active drug substance, the opioid may be selected from naturally occurring opioids, synthetic opioids and semisynthetic opioids.

In another embodiment, the active drug substance is selected from amfetamine, dexamfetamine, lisdexamfetamine, metamfetamine, methylphenidate, dexmethylphenidate and combinations thereof.

In some embodiments, the pharmaceutical compositions disclosed herein includes an opioid, the opioid is selected from buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol and dihydromorphine.

Where an opioid is used as an active drug substance, the opioid may be present in any of its crystalline, polymorphous, semi-crystalline, and amorphous or polyamorphous forms. Furthermore, in some embodiments, an opioid used as an active drug substance may be present in one or more forms selected from its crystalline, polymorphous, semi-crystalline, and amorphous or polyamorphous forms.

Specific embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts of any of the aforementioned, such as from the group consisting of oxycodone hydrochloride, hydrocodone bitartrate, hydromorphone hydrochloride and morphine sulphate pentahydrate.

In certain embodiments, the pharmaceutical compositions as described herein are suitable for use for water soluble as well as slightly soluble or insoluble active drug substances.

In some embodiments, all of the above mentioned active drug substances may also be in the form of pharmaceutically acceptable salts, uncharged or charged molecules, molecular complexes, solvates, or anhydrates thereof, and, if relevant, isomers, enantiomers, racemic mixtures, and mixtures thereof.

In particular embodiments, the pharmaceutical compositions described herein may comprise pharmaceutically acceptable salts of any of the above mentioned active drug substances.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methansulphonic acid, toluenesulphonic acid etc.

The term "pharmaceutically acceptable salts" of an opioid includes alkali metal salts such as, for example, sodium or potassium salts, alkaline earth metal salts such as, for example, calcium and magnesium salts, and salts with organic or inorganic acids such as, for example hydrochloric acid, hydrobromic acid, nitric acid, sulfuric acid, phosphoric acid, citric acid, formic acid, maleic acid, succinic acid, tartaric acid, methansulphonic acid, toluenesulphonic acid etc or tartrate acid. In particular embodiments, pharmaceutically acceptable opioid salts may be selected from the group consisting of sulphate salts, hydrochloride salts and bitartrate salts.

The term "solvates" includes hydrates or solvates wherein other solvates than water are involved such as, for example, organic solvents like chloroform and the like.

Furthermore, in some embodiments, the active drug substance may be in any of its crystalline, polymorphous, semi-crystalline, amorphous or polyamorphous forms and mixtures thereof.

The concentration of the active drug substance in the pharmaceutical composition for use according to the disclosure depends on the specific active drug substance, the disease to be treated, the condition of the patient, the age and gender of the patient etc. The above-mentioned active drug substances may be known active drug substances and a person skilled in the art will be able to find information as to the dosage of each active drug substance and, accordingly, will know how to determine the amount of each active drug substance in the pharmaceutical composition.

The active drug substance may be a new chemical entity for which the amount of information is limited. In such cases, the dosage has to be evaluated based on available preclinical and/or clinical data.

In some embodiments, the active drug substance is typically present in the composition in an amount of from 5 to about 90% w/w such as, for example, from about 5 to about 80% w/w, from about 5 to about 70% w/w, from about 5 to about 60% w/w, from about 5 to about 50% w/w, from about 5 to about 40% w/w, from about 5 to about 30% w/w, from about 5 to about 20% w/w, from about 5 to about 10% w/w.

In certain embodiments, when the active drug substance is an opioid, such as, for example, morphine, oxycodone, hydromorphone or oxymorphone or pharmaceutically acceptable salts thereof, then said opioid is typically present in the compositions in a concentration of in the range of 5 to 70% w/w, for example in the range of 5 to 60% w/w, such as in the range of 5 to 50% w/w, for example in the range of 5 to 45% w/w, such as in the range of 5 to 40% w/w, for example in the range of 5 to 35% w/w, such as in the range of 5 to 30% w/w, for example in the range of 5 to 25% w/w, such as in the range of 5 to 20% w/w, for example in the range of 5 to 15% w/w, such as in the range of 5 to 10% w/w.

In certain embodiments, the active drug substance is typically present in the composition in an amount of from 1 to about 90% w/w such as, for example, from about 1 to about 80% w/w, from about 1 to about 70% w/w, from about 1 to about 60% w/w, from about 1 to about 50% w/w, from about 1 to about 40% w/w, from about 1 to about 30% w/w, from about 1 to about 20% w/w, from about 1 to about 10% w/w.

In certain embodiments, when the active drug substance is an opioid, such as, for example, morphine, oxycodone, hydromorphone or oxymorphone or pharmaceutically acceptable salts thereof, then said opioid is typically present in the compositions in a concentration of in the range of 1 to 70% w/w, for example in the range of 1 to 60% w/w, such as in the range of 1 to 50% w/w, for example in the range of 1 to 45% w/w, such as in the range of 1 to 40% w/w, for example in the range of 1 to 35% w/w, such as in the range of 1 to 30% w/w, for example in the range of 1 to 25% w/w, such as in the range of 1 to 20% w/w, for example in the range of 1 to 15% w/w, such as in the range of 1 to 10% w/w.

In certain embodiments, the compositions comprise a load of the active drug substance, such as an opioid. A load is generally less than 50% w/w of the active drug substance. For example, in certain such embodiments, the compositions may include an active drug substance in an amount selected from less than 40% w/w and less than 30% w/w.

In some embodiments, a pharmaceutical composition as described herein may comprise one active drug substance or more than one different active drug substances. Typically, the amount of the active drug substance corresponds to a daily or part of a daily therapeutic dose.

In certain embodiments, the pharmaceutical composition provides for administration 1-6 times a day, normally 1-4 times daily, such as 1-3 times daily, such as 1-2 times daily or 1 time daily.

In one embodiment, the pharmaceutical composition provides for twice-daily administration. In another embodiment, the pharmaceutical composition provides for once-daily administration.

Pharmaceutically Acceptable Excipients

The pharmaceutical compositions described herein may also contain other excipients in order to achieve one or more desired properties, such as, for example, better stability of the active drug substance or the pharmaceutical composition itself, enhance the abuse-deterrent properties, loading of the active drug substance or delivery characteristics, such as release rate or release profile of an active drug substance. Further, in some embodiments, the compositions described herein may include excipients that facilitate manufacture and production of dosage forms such as, for example, tablets suitable for administration to individuals in need thereof.

In certain embodiments, a suitable pharmaceutically acceptable excipient for use in compositions according to the present description may be selected from fillers, diluents, disintegrants, glidants, pH-adjusting agents, viscosity adjusting agents, solubility increasing or decreasing agents, osmotically active agents and solvents.

In some embodiments, suitable excipients include conventional tablet or capsule excipients. These excipients may be, for example, diluents such as dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol or mixtures thereof; binders such as alginic acid, calcium alginate, sodium alginate, starch, gelatin, saccharides (including glucose, sucrose, dextrose and lactose), carboxymethylcellulose, methylcellulose, veegum, larch arabolactan, polyethylene glycols, ethylcellulose, water, alcohols, waxes, polyvinylpyrrolidone such as PVP K90 or mixtures thereof; lubricants such as talc, silicium dioxide, magnesium stearate, calcium stearate, stearic acid, hydrogenated vegetable oils, sodium benzoate, sodium chloride, leucine, carbowax 4000, magnesium lauryl sulfate, Sodium laurilsulfate, Stearyl alcohol, Polysorbate 20, Polysorbate 60, Polysorbate 80, Macrogol stearate, Macrogol lauryl ether, Stearoyl macrogolglycerides, Sorbitan stearate, Sorbitan laurate, Macrogol glycerol hydroxystearat, colloidal silicon dioxide and mixtures thereof, disintegrants such as starches, clays, cellulose derivatives including crosscarmellose, gums, aligns, various combinations of hydrogencarbonates with weak acids (e.g., sodium hydrogencarbonate/tartaric acid or citric acid) crosprovidone, sodium starch glycolate, agar, cation exchange resins, citrus pulp, veegum, glycollate, natural sponge, bentonite, sucralfate, calcium hydroxyl-apatite or mixtures thereof.

In certain embodiments, in addition to a polymer of a polyethylene oxide, the composition may comprise an additional polymer such as polyglycols selected from substantially water soluble, thermoplastic, crystalline, semi-crystalline or amorphous or a mixture of substantially water soluble, crystalline, semi-crystalline or amorphous polymers. In particular, in certain embodiments, the polyglycol is at least thermoplastic. Suitable polyglycols for use in the composition include, for example, polyethylene glycols (for example with a molecular weight below 35,000 daltons), as well as derivatives of polyethylene glycol, such as mono or dimethoxypolyethylene glycols (mPEGs), polyethylene oxides and/or block copolymers of ethylene oxide and propylene oxide.

In some embodiments, in addition to a polymer of a polyethylene oxide, the composition may comprise an additional polymer, such as, for example, at least one polymer selected from: modified or unmodified water soluble natural polymers such as glucomannan, galactan, glucan, polygalacturonic acid, polyxylane, polygalactomannans, rhanogalacturonan, polyxyloglycan, arabinogalactan, and starch, cellulose, chitosan, alginate, fibrin, collagen, gelatin, hyaluronic acid, amylopectin, pectin including low methylated or methoxylated pectins, dextran and fatty acids and alcohols; synthetic polymers such as Carbopol, carbomer, carbomer homopolymer, carboxyvinyl polymer, polyvinylpyrrolidone (PVP), PVA, PVB, Eudragit L methyl ester, Eudragit L, Eudragit RL, Eudragit RS, Eudragit E, Eudragit S, PHPV, PHA, PCL, PLGA and PLA; and hydrogels made from the polymers or combined polymers mentioned above and or from polymers originated from HEMA, HEEMA, MEMA, MEEMA, EDGMA, NVP, VAc, AA, acrylamide, MAA, HPMA, PEGA, PEGMA, PEGDMA, PEGDA, and PEGDMA.

In certain embodiments, the composition as described herein may comprise one or more gelling agents. Examples are polymers selected from the group consisting of modified or unmodified water soluble natural polymers such as glucomannan, galactan, glucan, polygalacturonic acid, polyxylane, polygalactomannans, polyxyloglycan, arabinogalactan, starch, cellulose, chitosan, alginate, fibrin, collagen, gelatin, amylopectin, pectin including low methylated or methoxylated pectins, dextran; synthetic polymers such as PVA and PVB; and hydrogels made from the polymers or combined polymers mentioned above and or from polymers originated from: HEMA, HEEMA, MEMA, MEEMA, EDGMA, NVP, VAc, AA, acrylamide, MAA, HPMA, PEGA, PEGMA, PEGDMA, PEGDA, and/or PEGDMA, hydroxypropyl cellulose, methylcellulose, hydroxyethyl cellulose, ethylcellulose, hydroxypropyl methylcellulose phthalate, hydroxypropyl methylcellulose acetate succinate or other cellulose derivates, carboxymethylcellulose sodium, carboxymethylcellulose calcium, carrageenans, guar gum, gellan gum, xanthan gum, tragacanth, and arabic gum.

In some embodiments, exemplary stabilizers (chemical) include TPG, for example, in the form of TPGS (Vitamin E Polyethylene glycol succinate) and BHT, BHA, t-butyl hydroquinone, butylhydroxy toluene, calcium ascorbate, gallic acid, hydroquinone, maltol, octyl gallate, sodium bisulfite, sodium metabisulfite, tocopherol and derivates thereof, citric acid, tartaric acid, and ascorbic acid. Other stabilisers include trivalent phosphorous, such as, for example, phosphite, phenolic antioxidants, hydroxylamines, lactones such as substituted benzofuranones, hindered phenols, thiosynergists and/or hindered amines, acids (ascorbic acid, erythorbic acid, etidronic acid, hypophosphorous acid, nordihydroguaiaretic acid, propionic acid etc.), phenols, dodecyl gallate, octyl gallate, 1,3,5-trihydroxybenzene, organic and inorganic salts (calcium ascorbate, sodium ascorbate, sodium bisulphite, sodium metabisulfite, sodium sulfite, potassium bisulphite, potassium metabisulphite), esters (calcium ascorbate, dilauryl thiodipropionate, dimyristyl thiodipropionate, distearyl thiodipropionate), pyranon (maltol), and vitamin E (tocopherol, D-[alpha]-tocopherol, DL-[alpha]-tocopherol, tocopheryl acetate, d-[alpha]-tocopheryl acetate, dl-[alpha]-tocopheryl acetate. However, other anti-oxidative agents known in the art may also be used. Other suitable stabilizers may be selected from, for example, sorbitol glyceryl tricitrate, and sucrose octaacetate.

In one embodiment, a composition as described herein comprises one or more stabilizers selected from above mentioned group of stabilizers. In one such embodiment, the composition comprises butylhydroxytoluene and/or TPGS as a stabilizer. In another such embodiment, the composition comprises gallic acid and/or ascorbic acid as a stabilizer.

In certain embodiments, a release modifier may be incorporated in a composition as described herein. A suitable release modifier may be selected from fatty acids and esters, fatty alcohols, cetyl alcohol, stearyl alcohol, mineral oils, hydrogenated vegetable oils, vegetable oils, acetylated hydrogenated soybean oil glycerides, Castor oil, phosphate esters, amides, phthalate esters, glyceryl cocoate oleyl alcohol, myristyl alcohol, sucrose octaacetate, diacetylated monoglycerides, diethylene glycol monostearate, ethylene glycol monostearate, glyceryl monooleate, glyceryl monostearate, propylene glycol monostearate, macrogol esters, macrogol stearate 400, macrogol stearate 2000, polyoxyethylene 50 stearate, macrogol ethers, cetomacrogol 1000, lauromacrogols, poloxamers, polyvinyl alcohols, sorbitan monolaurate, sorbitan monooleate, sorbitan monopalmitate, sorbitan monostearate, sorbitan sesquioleate, sorbitan trioleate, sorbitan tristearate, ethylcellulose, cellulose acetate, cellulose propionate, cellulose nitrate, cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxymethylcellulose and hydroxymethylpropylcellulose, cellulose acetate, polylactic acid or polyglycolic acid and copolymers thereof, methacrylates, a co-polymer of methacrylate-galactomannan etc., polyvinyl alcohols, glycerinated gelatine and cocoa butter.

In some embodiments, other suitable release modifiers may be selected from inorganic acids, inorganic bases, inorganic salts, organic acids or bases and pharmaceutically acceptable salts thereof, saccharides, oligosaccharides, polysaccharides, polyethylene glycol derivatives and cellulose and cellulose derivatives.

Alternatively or additionally, in particular embodiments, a composition according to the present description may include a pharmaceutically acceptable excipient selected from a mono-, di-, oligo, polycarboxylic acid or amino acids such as, for example, acetic acid, succinic acid, citric acid, tartaric acid, acrylic acid, benzoic acid, malic acid, maleic acid, sorbic acid etc., aspartic acid or glutamic acid etc.

In some embodiments, suitable organic acids that may be included in the compositions described herein include, for example, acetic acid/ethanoic acid, adipic acid, angelic acid, ascorbic acid/vitamin C, carbamic acid, cinnamic acid, citramalic acid, formic acid, fumaric acid, gallic acid, gentisic acid, glutaconic acid, glutaric acid, glyceric acid, glycolic acid, glyoxylic acid, lactic acid, levulinic acid, malonic acid, mandelic acid, oxalic acid, oxamic acid, pimelic acid, or pyruvic acid.

In certain embodiments, suitable inorganic acids that may be included in the compositions described herein include, for example, pyrophosphoric, glycerophosphoric, phosphoric such as ortho and meta phosphoric, boric acid, hydrochloric acid, or sulfuric acid.

In particular embodiments, examples of suitable inorganic compounds that may be included in the compositions described herein include, for example, aluminium, calcium or kalium.

In particular embodiments, examples of organic bases that may be included in the compositions described herein include, for example, p-nitrophenol, succinimide, benzenesulfonamide, 2-hydroxy-2cyclohexenone, imidazole, pyrrole, diethanolamine, ethyleneamine tris(hydroxymethyl) aminomethane, hydroxylamine and derivates of amines, sodium citrate, aniline or hydrazine. Examples of inorganic bases that may be included in the compositions described herein include, for example, aluminium oxide such as, for example, aluminium oxide trihydrate, alumina, sodium hydroxide, potassium hydroxide, calcium carbonate, ammonium carbonate, ammonium hydroxide or KOH.

In some embodiments, pharmaceutically acceptable salts of an organic acid that may be included in the compositions described herein include, for example, an alkali metal salt or an alkaline earth metal salt such as, for example, sodium phosphate, sodium dihydrogenphosphate, disodium hydrogenphosphate etc., potassium phosphate, potassium dihydrogenphosphate, potassium hydrogenphosphate etc., calcium phosphate, dicalcium phosphate etc., sodium sulfate, potassium sulfate, calcium sulfate, sodium carbonate, sodium hydrogencarbonate, potassium carbonate, potassium hydrogencarbonate, calcium carbonate, magnesium carbonate etc., sodium acetate, potassium acetate, calcium acetate, sodium succinate, potassium succinate, calcium succinate, sodium citrate, potassium citrate, calcium citrate, sodium tartrate, potassium tartrate or calcium tartrate.

In certain embodiments, suitable inorganic salts for that may be used in a composition as described herein include, for example, sodium chloride, potassium chloride, calcium chloride or magnesium chloride.

In some embodiments, the composition may comprise at least one saccharide. Where a saccharide is included in a composition as described herein, the saccharide may be selected from, for example, glucose, ribose, arabinose, xylose, lyxose, xylol, allose, altrose, inosito, glucose, sorbitol, mannose, gulose, glycerol, idose, galactose, talose, mannitol, erythritol, ribitol, xylitol, maltitol, isomalt, lactitol, sucrose, fructose, lactose, dextrin, dextran, amylase or xylan.

In certain embodiments, the composition may also comprise cellulose and/or cellulose derivatives selected from the group consisting of methylcellulose, carboxymethylcellulose and salts thereof, microcrystalline cellulose, ethylhydroxyethylcellulose, ethylcellulose, cellulose acetate, cellulose proprionate, cellulose nitrate, cellulose acetate phthalate, ethylmethylcellulose, hydroxyethylcellulose, hydroxyethylmethylcellulose, hydroxypropylcellulose, hydroxymethylcellulose and hydroxymethylpropylcellulose.

Furthermore, in particular embodiments, the compositions described herein may comprise one or more agents selected from sweetening agents, flavouring agents and colouring agents in order to provide an elegant and palatable preparation. Examples include maltol, citric acid, water soluble FD&C dyes and mixtures thereof with corresponding lakes and direct compression sugars such as Di-Pac from Amstar. In addition, coloured dye migration inhibitors such as; tragacanth, acacia or attapulgite talc may be added. Specific examples include calcium carbonate, 1,3,5-trihydroxybenzene, chromium-cobalt-aluminium oxide, ferric ferrocyanide, ferric oxide, Iron ammonium citrate, iron (III) oxide hydrated, iron oxides, carmine red, magnesium carbonate and titanium dioxide.

Preparation

The pharmaceutical compositions of the disclosure may be produced by various methods which are either known per se in the pharmaceutical industry or which, for example, are used in the production of polymer-based materials, depending upon the desired embodiment and the materials employed in the pharmaceutical composition in question. The pharmaceutical compositions according to the present description may be produced by methods that are relatively simple and inexpensive.

Suitable preparation methods for pharmaceutical compositions according to the present description include conventional tablet compression, hot melt-processing and other methods of preparing pharmaceutical compositions. In certain embodiments, hot melt-processing technology and the use of thermoplastic and thermosetting plastic polymers are able to give pharmaceutical compositions with low porosity, high viscosity and breaking strengths, like properties such as for example plastic which is difficult to tear down. In particular embodiments, a combination of one or more of the aforementioned methods may be employed for use in the preparation of pharmaceutical compositions disclosed herein.

In some embodiments, the pharmaceutical compositions described herein are prepared by hot melt-processing. In one such embodiment, the pharmaceutical compositions are prepared by, for example, 1, 2 or multiple component extrusion, molding, 1, 2 or multiple component injection molding. In another such embodiment, the pharmaceutical compositions are prepared by 1, 2 or multiple component injection molding.

In embodiments where a preparation is needed in order to make the pharmaceutical composition either before or after the above-mentioned preparation steps, the preparation may also comprise separate steps, such as, for example, wet granulation, dry granulation, melt granulation, pelletizing, curing, spray coating, electrostatic coating, dip coating or other forms of preparation methods.

In one embodiment, the pharmaceutical composition is prepared by conventional tablet compression.

In another embodiment, the pharmaceutical compositions are prepared by conventional tablet compression and hot melt processing.

Geometry

The pharmaceutical compositions according to the present description may be formed as cylindrical compositions. In certain embodiments, the pharmaceutical compositions are formed as a cylindrical shape optionally with one or two tapered end(s).

For purposes of the pharmaceutical compositions according to the present description, the cylindrical shape may be any geometrical shape having the same cross section area throughout the length of the geometrical shape. Within the present context, cross sections are perpendicular to the axis of the cylinder. By way of example, if the cylindrical shape is elongated then the cross sections are perpendicular to the longitudinal axis. Preferably, the cylindrical shape is elongated. The cross section of a cylinder within the meaning of the present disclosure may have any two-dimensional shape, for example the cross section may be circular, oval, parabola, hyperbola, rectangular, triangular, otherwise angular, star shaped or an irregular shape. Accordingly, the cylindrical shape may for example be an elliptic cylinder, a parabolic cylinder, a hyperbolic cylinder or a prism. A prism within the present context is a cylinder whose cross-section is a polygon.

In some embodiments, the pharmaceutical composition according to the present description may have any common tablet shapes. Exemplary tablet shapes may include, for example, standard convex, standard convex bisect not flush, standard convex quadrisect flush, standard convex straight-through bisect, compound cup, convex with bevel, flat-faced plain, flat-faced bevel-edged, flat-faced bevel-edged bisect, flat-faced bevel-edged quadrisect, flat-faced radius-edged, lozenge, modified ball, core rod type (hole in center), capsule, modified capsule, oval, bullet, arrowhead, triangle, arc triangle, square, pillow (arc square), rectangle, modified rectangle, diamond, pentagon, hexagon, octagon natural edge, heart, half moon and almond. A skilled person would know the various kinds of shape that a tablet may be formed in.

In a particular embodiment, the pharmaceutical composition is prepared for oral intake, preferably for oral intake by swallowing. Accordingly, the size of the pharmaceutical composition may be in a range that allows for oral intake by swallowing.

Cosmetic Coat

In some embodiments, the pharmaceutical composition according to the present description may also contain a cosmetic coat that fully covers the composition. In certain such embodiments, the cosmetic coat may be selected from the group consisting of taste-masking coats, coats with aqueous moisture barriers and/or oxidative barriers to improve the stability of the composition, and coat containing colouring agents, sweetening agents and/or flavouring agents in order to provide an elegant and palatable pharmaceutical composition and/or to easy distinguishable dose strengths.

It can be particularly useful to coat compositions having different dose strengths or active drug substances with cosmetic coats of different colours so that the different actives and dose strengths are easily distinguished.

In certain embodiments, the cosmetic coat contains an active drug substance.

Where provided, the cosmetic coat may, in particular embodiments, be easily soluble in aqueous media in order to facilitate contact of the composition with the surrounding aqueous media rapidly after administration. In one such embodiment, the cosmetic coat is dissolved within 30 minutes after immersed in aquesous medie such as, for example, phosphate buffer solution pH 6.8.

Administration

The pharmaceutical composition according to the present description can be designed for oral administration. For example, in certain embodiments, the pharmaceutical compositions may be produced as tablets, for oral intake by swallowing one or more intact tablets of the pharmaceutical composition.

A pharmaceutical composition as described herein may comprise one active drug substance or more than one different active drug substance.

In certain embodiments, a pharmaceutical composition containing an active drug substance according to the present description is typically formulated for oral administration. Due to the possibility of controlling the release rate of the active drug substance, in particular embodiments, the pharmaceutical composition may be adapted for oral administration 1-6 times a day, such as 1-4 times daily, including 1-3 times, 1-2 times or twice or once daily.

In some embodiments, the pharmaceutical compositions according to the present description can be prepared for delivery of the desired dosage of active drug substance. In particular embodiments, the dosage may be dependent on the individual to whom the pharmaceutical composition as described herein is being administered and the active drug substance.

In particular embodiments, the dosage for each administration, wherein dosages are in the range of 1 to 1,000 mg, such as in the range of 5 to 1,000 mg, for example in the range of 8 to 1,000 mg, such as in the range of 10 to 1,000 mg, for example in the range of 30 to 1,000 mg, such as in the range of 1 to 750 mg, for example in the range of 1 to 500 mg, such as in the range of 1 to 250 mg of an active drug substance. In certain such embodiments, the dosage for each administration is in a range selected from 5 to 500 mg and 5 to 250 mg of an active drug substance.

In some embodiments, when the active drug substance included in the pharmaceutical compositions is an opioid, the dosage may be selected from a range of 1 to 1000 mg, a range of 10 to 1000 mg, a range of 15 to 1000 mg, a range of 20 to 1000 mg, a range of 30 to 1000 mg, a range of 1 to 500 mg, a range of 1 to 250 mg, a range of 10 to 500 mg, a range of 15 to 500 mg, a range of 15 to 250 mg, a range of 20 to 500 mg, a range of 20 to 250 mg, a range of 30 to 500 mg, a range of 30 to 250 mg, a range of 10 to 200 mg, a range of 15 to 200 mg, a range of 20 to 200 mg, and a range of 30 to 200 mg of the opioid. In certain such embodiments, the pharmaceutical composition includes opioid or a pharmaceutically acceptable salt thereof as an active drug substance and the dosage is selected from 10, 15, 20, 30, 50, 60, 80, 100 or 200 mg. In certain such embodiments, the pharmaceutical composition includes morphine as an active drug substance and the dosage is selected from 10, 15, 20, 30, 50, 60, 80, 90, 100, 120, 180 or 200 mg.

In another embodiment, when the active drug substance included in the pharmaceutical compositions is an opioid, the dosage may be selected from a range of 1 to 1,000 mg, a range of 10 to 1,000 mg, a range of 1 to 500 mg, a range of 1 to 250 mg, a range of 10 to 500 mg, a range of 10 to 250 mg, a range of 1 to 150 mg, a range of 10 to 150 mg, a range of 1 to 100 mg a range of 10 to 100 mg, a range of 1 to 80 mg and a range of 10 to 80 mg of the opoid. In certain such embodiments, the pharmaceutical composition includes opioids or a pharmaceutically acceptable salt thereof as an active drug substance and the dosage is selected from 10, 15, 20, 30, 40, 60 or 80 mg. In certain such embodiments, the pharmaceutical composition includes hydrocodone as an active drug substance and the dosage is selected from 10, 15, 20, 30, 40, 60 or 80 mg. In another such embodiments, the pharmaceutical composition includes oxycodone as an active drug substance and the dosage is selected from 10, 15, 20, 30, 40, 60 or 80 mg.

In still another embodiment, when the active drug substance included in the pharmaceutical compositions is an opioid, the dosage may be selected from a range of 1 to 1,000 mg, a range of 8 to 1,000 mg, a range of 1 to 500 mg, a range of 1 to 250 mg, a range of 8 to 500 mg, a range of 8 to 250 mg a range of 1 to 100 mg, a range of 8 to 100 mg, a range of 1 to 75 mg, a range of 8 to 75 mg, a range of 1 to 64 mg and a range of 8 to 64 mg of the opioid. In certain such embodiments, the pharmaceutical composition includes opioids or a pharmaceutically acceptable salt thereof as an active drug substance and the dosage is selected from 8, 12, 16, 32 or 64 mg. In certain such embodiments, the pharmaceutical composition includes hydromorphone as an active drug substance and the dosage is selected from 8, 12, 16, 32 or 64 mg.

In still another embodiment, when the active drug substance included in the pharmaceutical compositions is an opioid, the dosage may be selected from a range of 1 to 1,000 mg, a range of 5 to 1,000 mg, a range of 1 to 500 mg, a range of 1 to 250 mg, a range of 5 to 500 mg, a range of 5 to 250 mg a range of 1 to 100 mg, a range of 5 to 100 mg, a range of 1 to 50 mg, a range of 5 to 50 mg, a range of 1 to 40 mg, and a range of 5 to 40 mg of the opioid. In certain such embodiments, the pharmaceutical composition includes opioids or a pharmaceutically acceptable salt thereof as an active drug substance and the dosage is selected from 5, 7.5, 10, 15, 20, 30 or 40 mg. In certain such embodiments, the pharmaceutical composition includes oxymorphone as an active drug substance and the dosage is selected from 5, 7.5, 10, 15, 20, 30 or 40 mg.

In particular embodiments, the above-mentioned dosages are relevant when the individual in need of treatment is a human being, such as an adult human being.

Individuals in Need of Treatment

In some embodiments, the pharmaceutical composition of the disclosure is prepared for administration to an individual in need thereof. In certain such embodiments, the individual may be a mammal, and in specific embodiments the individual is a human being.

In certain embodiments, the pharmaceutical composition is for treatment of pain and accordingly, the individual in need of treatment is an individual suffering from pain.

In certain embodiments, wherein the active drug substance is an opioid, then the pharmaceutical compositions are suitable for treatment of moderate to severe pain such as severe pain.

In some embodiments, examples of individuals, who may benefit from treatment with the pharmaceutical compositions according to the disclosure, include, for example, the following:

The individual may be an individual suffering from chronic pain, such as moderate to severe chronic pain;

The individual may be an individual suffering from cancer and the pharmaceutical composition may be useful for continuous treatment of pain or even moderate to severe pain, such as severe pain in an individual suffering from cancer;

The individual may also be an individual who has suffered a moderate to severe injury;

The individual may be an individual suffering from pain associated with surgical conditions, such as a pre-surgical individual (an individual in need of surgery) or a post surgical individual (an individual who has undergone surgery);

The individual may also be an individual suffering from or having suffered from a myocardial infarction, sickle cell crises, kidney stone or severe back pain;

The individual may also be an individual suffering from degenerative pain, herniated disc pain, fibromyalgia, neuropathic pain and/or nociceptive pain; and The individual may also be an individual suffering from arthritis, such as arthritis osteo, arthritis rheumatoid, arthritis psoriatica and/or arthritis urica.

No Alcohol-Induced Dose Dumping

The pharmaceutical compositions according to the present description may be formulated or configured to provide a reduced risk for alcohol-induced dose dumping.

In specific embodiments, the pharmaceutical compositions according to the present description may be formulated or configured such that the pharmaceutical composition does not exhibit alcohol induced dose-dumping. In such embodiments, the composition exhibits a solubility and/or active drug substance release rate in alcohol containing media (for example, ethanol containing media) that is lower than or equal to the solubility and/or release rate in aqueous media that does not include alcohol (for example, water, phosphate buffer medium pH 6.8 or dilute hydrochloric acid). In some such embodiments, the polyethylene oxide and excipients selected for use in the pharmaceutical composition are provided in relative amounts that result in an unchanged or lower dissolution rate and/or release rate of the active drug substance in alcohol containing media (for example, ethanol containing media) as compared to the solubility and/or release rate exhibited in aqueous media that does not include alcohol (for example, water, phosphate buffer medium pH 6.8 or dilute hydrochloric acid). In certain such embodiments, the dissolution and/or release rate of the active drug substance from the pharmaceutical composition in alcohol containing media (for example, ethanol containing media) is at least 1.25 times lower, such as at least 1.5 times lower, such as at least 2 times lower, such as at least 5 times, such as at least 10 times lower than the dissolution and/or release rate of the active drug substance in aqueous media that does not include alcohol (for example, water, phosphate buffer medium pH 6.8, dilute hydrochloric acid, and the like).

More specifically, in some embodiments, the pharmaceutical composition may be formulated or configured to mitigate or prevent alcohol-induced dose dumping. In certain embodiments, the solubility or release rate of the composition is lower or substantially the same in alcohol than that in water. In certain such embodiments, the solubility or release rate of the composition is equal or at least 1.25 times lower such as at least 1.5 times lower; at least 2 times lower in alcohol than in water, notably 5 times or 10 times lower.

In particular embodiments, the pharmaceutical compositions according to the present description may be configured or formulated to mitigate or prevent alcohol-induced dose dumping. In certain such embodiments, the pharmaceutical compositions are formulated such that the ratio ($R_{50}$) between $t_{50\%}$ w/w (40% v/v ethanol in medium 1) and $t_{50\%}$ w/w (medium 1) is 1 or more. $t_{50\%}$ w/w (medium 1) denotes the time it takes to release 50% w/w of the active drug substance from the pharmaceutical composition in an in vitro dissolution test according to USP 35, NF 30, (711), Apparatus 2, paddle employing water optionally buffered to a specific pH as dissolution medium (medium 1), and $t_{50\%}$ w/w (40% v/v ethanol in medium 1) denotes the time it takes to release 50% w/w of the active drug substance from the pharmaceutical composition in an in vitro dissolution test according to USP 35, NF 30, (711), Apparatus 2, paddle employing 40% v/v ethanol in medium 1 as dissolution medium.

In certain embodiments, the ratio $R_{50}$ is at the most 3 or at the most 2. Notably, in certain such embodiments, the ratio $R_{50}$ provided by the pharmaceutical compositions described herein is from 1 to 1.5 such as, for example, from 1 to 1.4, from 1 to 1.3, from 1 to 1.2, from 1 to 1.1, from 1 to 1.05, about 1, from 1 to 0.95 or from 1 to 0.9.

In particular embodiments, the same may also apply for ratios determined, for example, when 25%, 30%, 40%, 60%, 70%, 80%, 90% and/or 95% w/w has been released, the conditions being as described above.

Abuse-Deterrent

The pharmaceutical compositions according to the present description are abuse-deterrent such that abuse administration is reduced, prevented or avoided. Abuse administration typically includes injection and/or snorting.

Injection may be avoided by providing a non-injectable composition having such high viscosity that injection is difficult or impossible, because a liquid solution cannot be obtained.

The term "non-injectable composition," as used herein, refers to pharmaceutical compositions having a viscosity of at least 95 mPa·s, for example at least about 100 mPa·s, such as at least about 105 mPa·s, for example at least about 110 mPa·s, such as at least about 120 mPa·s, for example at least about 130 mPa·s, such as at least about 140 mPa·s, for example at least about 150 mPa·s, such as at least about 160 mPa·s, for example, at least about 170 mPa·s, such as at least about 180 mPa·s, for example at least about 190 mPa·s, such as at least about 200 mPa·s. for example at least about 220 mPa·s, such as at least about 240 mPa·s, where the viscosity is measured according to "Viscosity Test #2," described in the "Viscosity test" disclosure. In particular embodiments, the term "non-injectable composition," as used herein, refers to pharmaceutical compositions having a viscosity of at least 170 mPa·s, where the viscosity is measured according to "Viscosity Test #2," described in the "Viscosity test" disclosure.

Furthermore, the term "non-injectable composition," as used herein, may also refer to pharmaceutical compositions having a viscosity in a range selected from between about 0.5 Pa·s to about 3,000 Pa·s, between about 0.5 Pa·s to about 2,500 Pa·s, between about 0.5 Pa·s to about 2,000 Pa·s, between about 0.5 Pa·s to about 1,700 Pa·s, between about 5 Pa·s to about 3,000 Pa·s, between about 10 Pa·s to about 3,000 Pa·s, between about 20 Pa·s to about 3,000 Pa·s, between about 30 Pa·s to about 3,000 Pa·s, between about 40 Pa·s to about 3,000 Pa·s, between about 45 Pa·s to about 3,000 Pa·s, between about 45 Pa·s to about 2,500 Pa·s, between about 45 Pa·s to about 2,000 Pa·s, between about 45 Pa·s to about 1,700 Pa·s, between about between about 46 Pa·s to about 1,700 Pa·s, where the viscosity is measured according to "Viscosity Test #1," described in the "Viscosity test" disclosure. In particular embodiments, the term "non-injectable composition," as used herein, refers to pharmaceutical compositions having a viscosity of at least about 46 Pa·s, where the viscosity is measured according to Viscosity Test #1, described in the "Viscosity test" disclosure.

Snorting may be avoided by providing a non-snortable composition, which cannot be tampered into small particles or powder form such that snorting is made impossible.

In certain embodiments of the pharmaceutical compositions described herein, the term "non-snortable composition" refers to compositions wherein at least 90 wt % of the particles obtained after physical tampering of the composition is larger than about 1,050 μm, such as larger than about 1,100 μm, such as larger than about 1,150 μm. In particular embodiments, the term "non-snortable composition," as used herein, refers to a composition where at least 90 wt % of the particles obtained after physical tampering of the pharmaceutical composition is larger than 1,100 μm.

In certain circumstances, an abuser may tamper with pharmaceutical compositions in a manner or by using a method that achieves maximal size reduction of the pharmaceutical composition in a minimal amount of time, while obtaining small particles, a powder, or other similar products, which can be dissolved or administered as easily as possible.

A series of abuse or tampering methods have been developed to illustrate the extent of the pharmaceutical compositions described herein of being abuse-deterrent.

If a pharmaceutical composition disintegrates into particles, then it may be possible to dissolve or suspend the particles and use them for abuse purposes. Moreover, if it is possible to disintegrate (e.g., crush) a pharmaceutical composition, then it is possible to use the powder for snorting or sniffing and, in this way, abuse the composition. However, if it is not possible to crush a pharmaceutical composition, then there will be no particles to use for such abuse purposes. In particular embodiments, the pharmaceutical compositions described herein cannot be crushed into particles by the apparatus (e.g., tablet hardness tester) specified in Ph. Eur.

A particle size reduction test method has been developed to evaluate abuse potential when the pharmaceutical composition is subjected to physical tampering.

In some embodiments, a pharmaceutical composition is abuse-deterrent, provided that the pharmaceutical composition does not change its release profile from a controlled release to an immediate release of the active drug substance subsequent to physical tampering (e.g., particle size reduction test, where the test program is successfully completed), which indicates that the pharmaceutical composition is abuse-deterrent. In some such embodiments, tests on a pharmaceutical composition subjected to physical tampering may also result in equipment failure, and in such an instance, the test program is considered successfully completed, indicating a pharmaceutical composition as abuse-deterrent.

If a pharmaceutical composition is crushed or broken into small pieces or small particles, an increased exposed surface area is created, which may increase the release rate of the active drug substance. Such an increase in release rate may lead to an increased potential for abuse. If a change in the release profile of the active drug substance from a controlled release to an immediate release is noticed, the pharmaceutical composition is considered to have failed. At such a point, the pharmaceutical composition is considered to have potential for abuse, such as by snorting or chemical extraction and it is evaluated. If the active drug substance can be extracted from the compromised pharmaceutical composition, the ease with which such extracted active drug substance can be injected is evaluated.

Crisping

The crisping test methods as described herein include methods intended to circumvent the controlled release mechanism in or interfere with the controlled release profile of a pharmaceutical composition. Crisping is a heating process designed to remove, reduce, or degrade at least some of the unwanted or undesired excipients contained within a dosage form and make the dosage form easier to abuse the active drug substance. Crisping may be employed to make it easier to crush the composition into small particles or a powder form so that snorting is made possible, or to make it easier to dissolve the composition into an injectable liquid solution, dispersion, or suspension.

Crisping or heating methods, such as, for example, heating in an oven, a microwave oven, a spoon over an open flame, and the like, may be employed by a potential abuser to it make it easier to reduce the particle size and/or the viscosity of the pharmaceutical compositions. The heating is normally stopped when the pharmaceutical composition starts to turn a brown colour. Further processes designed to facilitate or enable abuse such as, for example, particle size reduction, extraction and/or injection are typically initiated after the crisping process is completed.

In certain embodiments, the pharmaceutical compositions according to the present description are not made easier to crush into snortable particles or powder form or to dissolve into an injectable liquid solution by crisping. In certain embodiments, stearate may be added to the pharmaceutical composition as described herein to facilitate the colour change of the composition to a brown and/or dark colour or even to facilitate the composition burning when exposed to a crisping process. In a particular embodiment, the stearate added is magnesium stearate, calcium stearate and/or stearic acid.

Particle Size Reduction

The particle size reduction test methods described herein include methods for reducing the particle size of the pharmaceutical compositions via physical tampering, such as, for example, crushing, hammering, chopping, grinding, grating, cutting, and other means of particle size reduction.

The particle size reduction test can be carried out using a number of mechanical and electrical tools that are common household items or are readily commercially available. Tools that may be used in carrying out particle size reduction testing include, for example, a mortar and pestle, a hammer, a grater, a food chopper, a coffee grinder, and the like.

Pharmaceutical compositions and dosage forms (including, for example, tablets), that have been subjected to physical tampering may be further analyzed by use of image processing and/or particle size analysis. Pharmaceutical compositions subjected to physical tampering may be analyzed by collecting the different fractions and analyzing, such as, for example, by weighing and/or dissolving to assess the contents of active drug substance in the different fractions and/or to assess the dissolution rate. For comparison, a control dissolution test as described in the "Dissolution test" disclosure may be performed using intact tablets (e.g., tablets that have not been subjected to physical tampering), and the results from the control dissolution test may be used as control data.

Extraction

The extraction test methods described herein include methods for evaluating the extractability of active drug substance(s) from pharmaceutical compositions in different types of solvents. The extraction test can be carried out using approximately 3 ml of water to prepare a solution of, for example, MS Contin® for injection.

Shaking

Different amount of solvents and ways of handling the solutions have been tested. In certain embodiments, in order to ensure that as much as possible of the active drug substance has been extracted, shaking is selected as an extraction method. In certain such embodiments, extraction of an active drug substance from a pharmaceutical composition may be facilitated by placing a pharmaceutical composition in at least one solvent and shaking the pharmaceutical composition and the at least one solvent.

In particular embodiments, in order to ensure that as much as possible of the active drug substance has been extracted, continuous shaking is selected as an extraction method. In one embodiment, extraction of an active drug substance from a pharmaceutical composition may be facilitated by placing a pharmaceutical composition in at least one solvent and continuously shaking the pharmaceutical composition and the at least one solvent. In some embodiments, "continuous shaking," as used herein, refers to shaking for at least 1 second, for at least 5 seconds, for at least 30 seconds, for at least 1 min, for at least 5 minutes, for at least 10 minutes, for at least 15 minutes, for at least 30 minutes, for at least 45 minutes, for at least 60 minutes, for at least 2 hours, for at least 4 hours, for at least 8 hours, for at least 12 hours, for at least 24 hours, for at least 2 days, for at least 3 days, for at least 4 days, for at least 5 days, for at least 6 days, for at least 1 week, for at least 2 weeks, for at least a month.

Unshaken/Undisturbed

In another embodiment, as an extraction method, the pharmaceutical composition may be placed in at least one solvent and left unshaken and/or undisturbed for a period of time. In certain embodiments, the pharmaceutical composition may be placed in at least one solvent and left unshaken and/or undisturbed for at least 4 hours, at least 8 hours, at least 12 hours, at least 24 hours, at least 48 hours, and at least 72 hours. In certain such embodiments, the pharmaceutical composition may be placed in at least one solvent and left unshaken and/or undisturbed, and the active drug substance in the solvent may be first measured after at least 24 hours.

The amount of active drug substance in the solvent may be measured at select time points within the first 60 minutes. In some embodiments, the amount of active drug substance in the solvent may be measured at least one time, at least two times, at least three times, at least four times, at least five times, and at least six times, within the first 60 minutes of placing the pharmaceutical composition in the at least one solvent. In particular embodiments, the amount of active substance in the solvent may be measured at least one time, at least two times, at least three times, at least four times, at least five times, and at least six times, within the first 24 hours of placing the pharmaceutical composition in the at least one solvent. In an embodiment, the amount of active drug substance in the solvent may be measured at at least three time points within the first 60 minutes, so as to evaluate the rate at which the active drug substance is released into the solvent.

Extraction of active drug substance from pharmaceutical compositions can be performed by dissolving, for example, tablets in different types of solvents. In particular embodiments, the tablets in different solvents may be shaken and/or continuous shaken. In other embodiments, the tablets in different solvents may be unshaken or undisturbed. The solvents can be chosen to cover a broad range of liquids with low and high pH, with some being some polar and some non-polar. In certain embodiments, the solvents may be categorized into five groups: such as for example, aqueous solutions, such as, for example, solution pH 1.2; buffer pH 6.8; buffer pH 10.0; water; and water+ethanol (40% v/v); beverages, such as, for example; Coca-Cola®; quinine containing soft drinks, such as, for example; tonic water and bitter lemon; Coca-Cola®+ ethanol (40% v/v); and vodka; common household liquids, such as, for example, 1% acetic acid; ethanol; methylethylketone; and acetone.

In some embodiments, it has been shown to be difficult to extract active substances from the pharmaceutical composition described herein in solvents such as beverages. In certain such embodiments, it has been shown to be difficult to extract active substances from the pharmaceutical composition described herein in solvents such as carbonated and/or soft drinks, including Coca-Cola®, and the like.

Injection

The injection test methods described herein include methods for evaluating the abuse potential of active drug substance from pharmaceutical compositions both quantitatively (i.e., such as, for example, time, yield, and unit operations required) and qualitatively (i.e., such as, for example, appearance).

In some embodiments, the general strategy behind the injection test methods, as described herein, is to mimic the actual procedures applied by drug abusers when preparing a pharmaceutical composition for injection and injecting it. In some such embodiments, the study design is therefore divided into three parts, such as, for example, preparation, filtration, and injection.

In certain embodiments, the objective is to record the time and effort required to prepare a solution or dispersion that can be used for injection and the obtained yield of the active drug substance. As described herein, drug abusers are, typically, only prepared to spend a limited amount of time for preparing a pharmaceutical composition for abuse. In certain such embodiments, all of the tests disclosed herein can be performed in an aqueous media, which is a commonly-used solvent for injection. Finally, the appearance of the resulting solution/dispersion is assessed in order to evaluate the likelihood that a drug abuser would inject the resulting injectable mass.

In certain embodiments, the pharmaceutical compositions described herein have predominantly high viscous properties analogous to plastic. In an aqueous medium or in the gastrointestinal tract, the pharmaceutical compositions described herein transforms from having high viscous properties to having predominately elastic properties that control the release rate of active drug substance, and which resist rapid extraction and/or injection. In particular embodiments, the predominately elastic properties of the pharmaceutical compositions in an aqueous medium or in the gastrointestinal tract provides a controlled-release profile of the active drug substance in an individual.

The high viscosity of the composition turns not only the composition into a non-injectable dispersion/gel, but also significantly delays the solubility of the composition to completely form into a gelatinous mass. In some embodiments, the high viscosity of the composition turns not only the composition into a non-injectable dispersion/gel, but also significantly deters the abuse of the pharmaceutical composition by eluting at least one polymer from the composition into the solvent, which turns the solvent into a gelatinous mass. In some such embodiments, the at least one polymer is a polyethylene oxide. In certain embodiments, the average molecular weight of the at least one polyethylene oxide eluting from the composition into the solvent is less than 5,000,000 daltons, for example less than 4,000,000 daltons, such as less than 3,000,000 daltons, for example less than 2,000,000 daltons, such as less than 1,000,000 daltons, for example less than 800,000 daltons, such as less than 600,000 daltons, for example less than 500,000 daltons.

In particular embodiments, the high viscosity of the composition is in a range selected from between about 0.5 Pa·s to about 3,000 Pa·s, between about 0.5 Pa·s to about 2,500 Pa·s, between about 0.5 Pa·s to about 2,000 Pa·s, between about 0.5 Pa·s to about 1,700 Pa·s, between about 5 Pa·s to about 3,000 Pa·s, between about 10 Pa·s to about 3,000 Pa·s, between about 20 Pa·s to about 3,000 Pa·s, between about 30 Pa·s to about 3,000 Pa·s, between about 40 Pa·s to about 3,000 Pa·s, between about 45 Pa·s to about 3,000 Pa·s, between about 45 Pa·s to about 2,500 Pa·s, between about 45 Pa·s to about 2,000 Pa·s, between about 45 Pa·s to about 1,700 Pa·s, between about between about 46 Pa·s to about 1,700 Pa·s, where the viscosity is measured according to "Viscosity Test #1," described in the "Viscosity test" disclosure. In a specific embodiment, the viscosity of the composition at least about 46 Pa·s, where the viscosity is measured according to Viscosity Test #1, described in the "Viscosity test" disclosure.

In certain embodiments, the high viscosity of the composition is at least 95 mPa·s, for example at least about 100 mPa·s, such as at least about 105 mPa·s, for example at least about 110 mPa·s, such as at least about 120 mPa·s, for example at least about 130 mPa·s, such as at least about 140 mPa·s, for example at least about 150 mPa·s, such as at least about 160 mPa·s, for example, at least about 170 mPa·s, such as at least about 180 mPa·s, for example at least about 190 mPa·s, such as at least about 200 mPa·s. for example at least about 220 mPa·s, such as at least about 240 mPa·s, where the viscosity is measured according to "Viscosity Test #2," described in the "Viscosity test" disclosure. In particular embodiments, the high viscosity of the composition is at least 170 mPa·s, where the viscosity is measured according to "Viscosity Test #2," described in the "Viscosity test" disclosure.

The high viscosity of the composition deters direct injection and also serves as a significant barrier to prevent volatilization (e.g., inhalation) of the incorporated active drug substance at elevated temperature or snorting if the composition is crushed or broken into small pieces or small particles. In certain embodiments, the composition results in a highly viscous and/or unclear, opaque or cloudy dispersion/gel upon contact with and/or immersion in an aqueous medium, which may form a strong adhesion to the nose and nasal tissue walls and, thereby, result in discomfort in the nasal cavity of the abuser.

In some embodiments, it has been shown to be difficult to inject the abuse-deterrent pharmaceutical composition when the viscosity of the composition is at least 46 Pa·s, where the viscosity is measured according to Viscosity Test #1, described in the "Viscosity test" disclosure.

In certain embodiments, it has been shown to be difficult to inject the abuse-deterrent pharmaceutical composition when the viscosity of the composition is at least 100 mPa·s, where the viscosity is measured according to "Viscosity Test #2," described in the "Viscosity test" disclosure.

In some embodiments, the abuse-deterrent pharmaceutical compositions, as described herein, may form a gel that resists passage or is difficult to inject through a needle.

In further embodiments, the abuse-deterrent pharmaceutical compositions, as described herein, may further include a viscosity increasing agent, such as, for example, a gelling agent, and the like.

EXAMPLES

Certain embodiments of the disclosure are further illustrated in the following non-limiting examples.

Dissolution Test

Dissolution tests were performed in accordance with USP 35, NF 30, (711), Apparatus 2 (paddle method). The dissolution medium consisted either of phosphate buffer solution pH 6.8 with/without ethanol or of dilute hydrochloric acid with/without ethanol. The volume of the dissolution medium was 900 ml and the rotation speed of the paddles was 50 rpm or 75 rpm throughout the dissolution run. Samples were withdrawn at suitable time intervals and analysed for content of active drug substance by means of UV-detector or HPLC with UV-detector.

Dissolution Test (Immediate Release)

For the immediate-release test, the dissolution medium consisted of dilute hydrochloric acid. The volume of the dissolution medium was 900 ml and the rotation speed of the paddles was 75 rpm throughout the dissolution run.

Dissolution Test (Controlled Release)

For the controlled-release test, the dissolution medium consisted of phosphate buffer solution pH 6.8. The volume of the dissolution medium was 900 ml and the rotation speed of the paddles was 50 rpm throughout the dissolution run.

No Alcohol-Induced Dose Dumping Test

For the no alcohol-induced dose dumping test, the dissolution medium consisted of phosphate buffer solution pH 6.8 with/without 40% v/v ethanol. The volume of the dissolution medium was 900 ml and the rotation speed of the paddles was 50 rpm throughout the dissolution run.

Crisping Test

Three (3) whole tablets were placed in a 50 ml glass bottle. The bottle was placed in the center of a microwave oven and heated for a predetermined amount of time (e.g., 8 and 16 minutes) at maximum effect (900 W). Afterwards, 9 ml of purified water was added to the bottle. The bottle was placed on a flatbed laboratory shaker (IKA-Werke HS-501 digital) and was shook continuously (speed 150/min) for 3 days at ambient temperature to dissolve the tablets and to reduce clumping.

Viscosity Test

Four (4) tablets were weighed and placed in a bottle with 12 ml purified water. The bottle was placed on a flatbed laboratory shaker (IKA-Werke HS-501 digital) and was shook continuously (speed 150/min) for 3 days at ambient temperature to dissolve the tablets and to reduce clumping.

Viscosity can be measured using a Brookfield RVDV-E viscometer (Brookfield Engineering, Middleboro, Mass. USA) with spindle number 15 (0.5-1700 Pa·s), a 7R tube, a small sample adapter SC4-45Y and tested in the range of 1, 5, 10 and 20 rpm, respectively, or with spindle number 21 (0.05-170 Pa·s), a 13R tube, and a small sample adapter SC4-45Y at 20 rpm. The temperature was controlled and in the range of 21-22° C.

Viscosity Test #1

In one viscosity test (Viscosity Test #1), the viscosity can be measured using a Brookfield RVDV-E viscometer (Brookfield Engineering, Middleboro, Mass. USA) with spindle number 15 (0.5-1700 Pa·s), a 7R tube, and a small sample adapter SC4-45Y at 5 rpm. The temperature was controlled and in the range of 21-22° C.

Viscosity Test #2

In another viscosity test (Viscosity Test #2), the viscosity can be measured using a Brookfield RVDV-E viscometer (Brookfield Engineering, Middleboro, Mass. USA) with spindle number 21 (0.05-170 Pa·s), a 13R tube, and a small sample adapter SC4-45Y at 20 rpm. The temperature was controlled and in the range of 21-22° C.

Particle Size Reduction Test

Particle size reduction of pharmaceutical compositions was tested using a coffee grinder and/or a nutmeg grater. The methods described herein are used to evaluate the efforts required to reduce the particle size of the pharmaceutical compositions via physical grinding or grating of the tablets.

Figure 2:
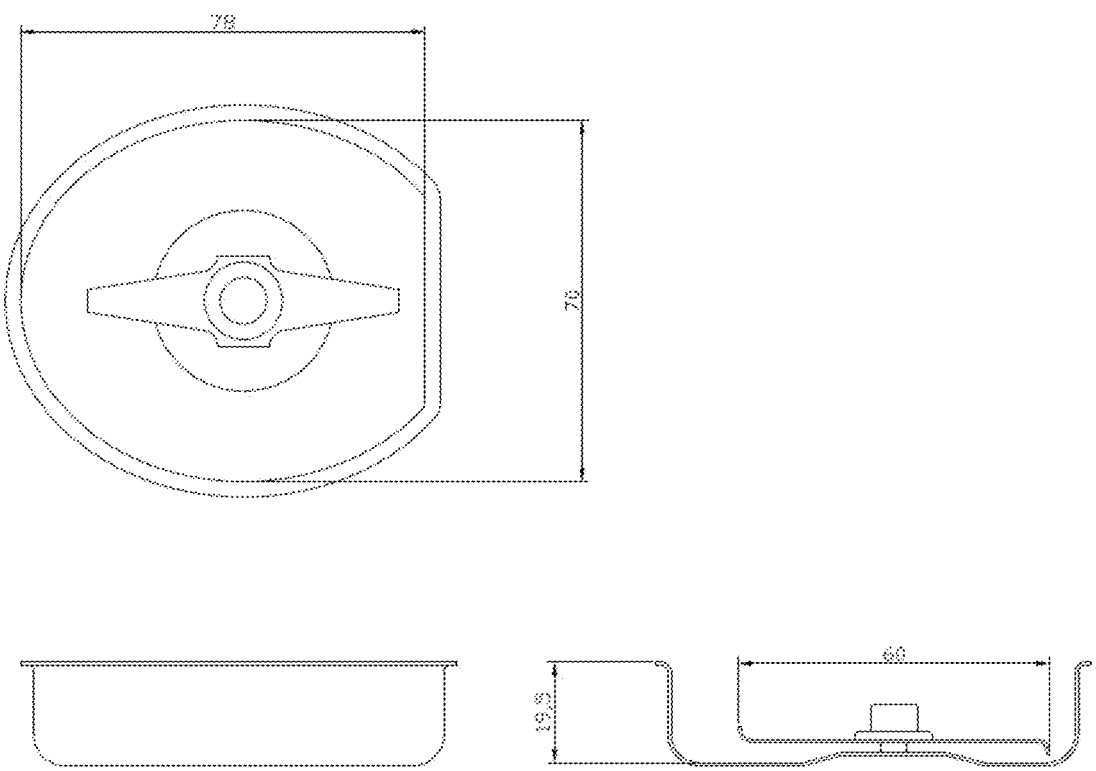
FIG. 2 shows a drawing of a Krups F203 coffee grinder chamber with stainless steel blades.

Tablets were ground in either a Moulinex-1411R coffee grinder with stainless steel blades (model: the original grinder; 50 g—180 W AR100G31/6WO) at 10 000-20 000 rpm or a Krups F203 coffee grinder with stainless steel blades (Model: 75 g—200 W F2034210/6WO-1512 R) at 30 000-50 000 rpm for 15 seconds or to no more particle size reduction or equipment failure and, afterwards, analyzed by use of Image Processing. A drawing of the coffee grinder chamber is shown in FIGS. 1 and 2.

Figure 3:
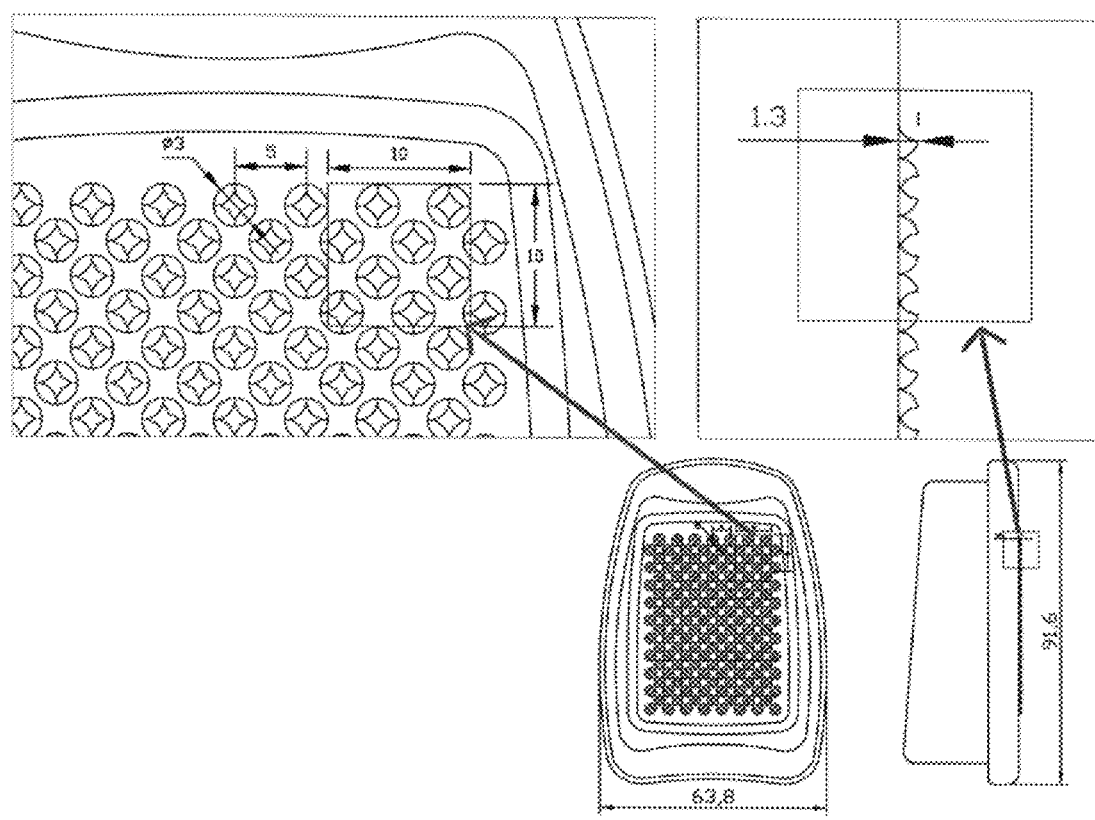
FIG. 3 shows a drawing of a nutmeg grater surface with a stainless steel star blade.

Tablets were grated by using a nutmeg grater with a stainless steel star blade or a Microplane® grater with stainless steel zester grater or a fine or spice blade for 1½ minutes. A drawing of the nutmeg grater with stainless steel star blade is shown in FIG. 3.

The samples were analyzed using an image processing setup comprising a digital SLR with RAW or TIFF capabilities (Canon EOS 350D, resolution 3466×2306 (8 MP) or Nikon D3100, resolution 4608×3272 (14.2 MP)), a fixed lens (Canon EF 100 mm 1:2:8 USM Macro or Tamron 90 mm 1:2:8 Macro), a stable camera stand, a suitable background for the particles (e.g., a black paper square) and light (to avoid reflections) plus a calibrated light microscopy scale bar from Leitz.

A sample was spread onto the black background, and the particles were separated. The position of the camera setup was adjusted and focused such that entire sample was inside the approximate view-area for the camera before pictures were taken.

Data were processed by using the software: RawTherapee 3.0.1.0 (Conversion of RAW-files to uncompressed TIFF.), ImageJ 1.45b (Thresholding of TIFF images (binarization) and particle size measuring (data rendering)) and Microsoft Excel 2010 (data analysis).

Preparation of Pharmaceutical Compositions

A general method for the preparation of a pharmaceutical composition, as disclosed herein, is described below.

An accurate amount of the polymer (i.e., in the examples below: polyethylene oxide) is loaded into a MTI mixer followed by an accurate amount of the active drug substance and/or plasticizer and/or other pharmaceutically acceptable excipient(s), if any. The mixing is performed at 900-2000 rpm and at a time period up to 20 min. At the start of the mixing the temperature is about 19-21° C. and the final temperature of the mixture is about 30-50° C. The mixture is then allowed to cool to room temperature and is ready to be fed into an injection moulding machine. The injection moulding machine used is an Arburg Allrounder 420 C 1000-60/60.

Example 1

Preparation of a Pharmaceutical Composition Containing PEO 400,000 for Use According to the Disclosure A composition (batch No. 1577-051A) according to the disclosure was prepared from the following ingredients:

| Composition | mg |
| --- | --- |
| PEO 400,000 | 436.2 |
| Poloxamer 188 | 116.3 |
| Morphine Sulphate Pentahydrate | 29.1 |

The composition was prepared as described above.

Figure 4:
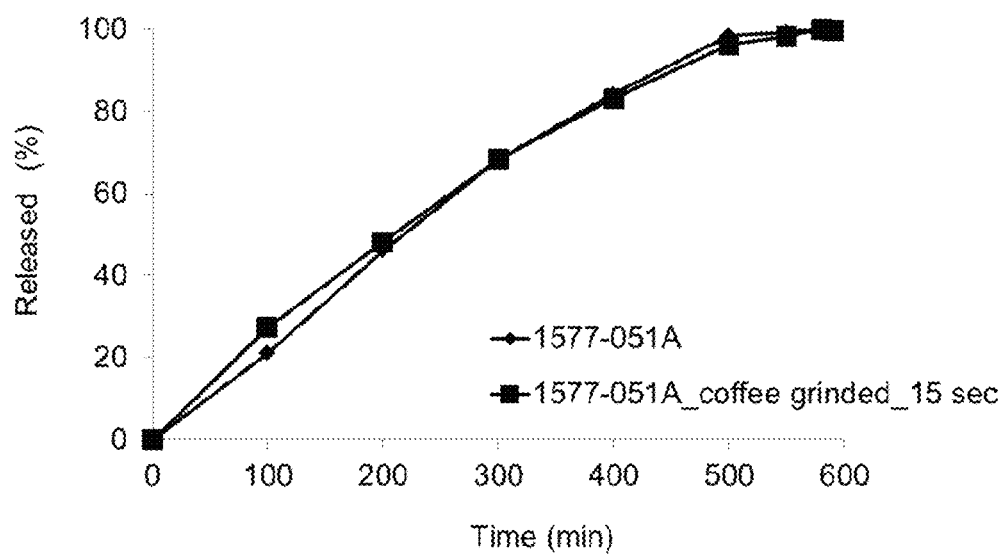
FIG. 4 shows in vitro dissolution results of the release of morphine (%) versus time (minutes) in phosphate buffer solution pH 6.8. The release of morphine is shown for intact tablets (untampered) and ground tablets (tampered) of one embodiment of a pharmaceutical composition, as disclosed herein, comprising PEO 400,000 daltons.

The composition was subjected to the dissolution test (controlled release) described above. The results are shown in FIG. 4 as the release of morphine (%) versus time (minutes) in phosphate buffer solution pH 6.8. The release of morphine is shown for intact tablets and ground tablets (ground in a Moulinex-1411R coffee grinder).

The viscosity of the composition was measured as described above. The viscosity was found to be 93 Pa·s at 5 rpm (using Viscosity Test #1).

Figure 5:
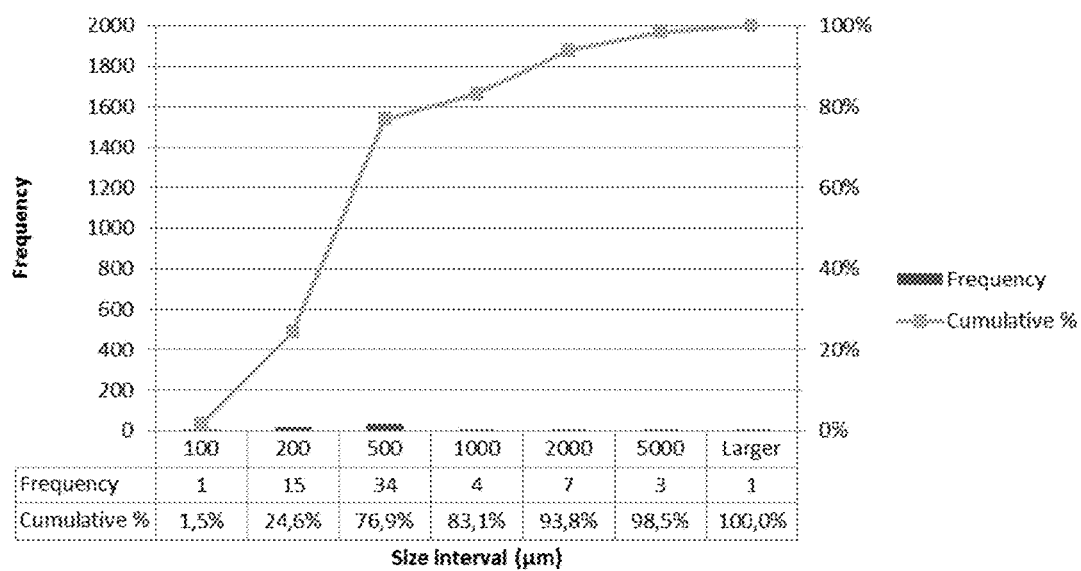
FIG. 5 shows particle size reduction results of one embodiment of a ground (tampered) pharmaceutical composition, as disclosed herein, comprising PEO 400,000 daltons.

Particle size reduction of the composition was measured as described above. The average particle size was 0.706±1.63 mm and the five largest particles were; 12.1 mm; 3.0 mm; 2.7 mm; 2.2 mm; and 1.9 mm. The results are shown in FIG. 5.

Example 2

Preparation of a Pharmaceutical Composition Containing PEO 600,000 for Use According to the Disclosure A composition (batch No. 1577-051B) according to the disclosure was prepared from the following ingredients:

| Composition | mg |
| --- | --- |
| PEO 600,000 | 348 |
| Poloxamer 188 | 93 |
| Oxycodone HCl | 23.25 |

The composition was prepared as described above.

Figure 6:
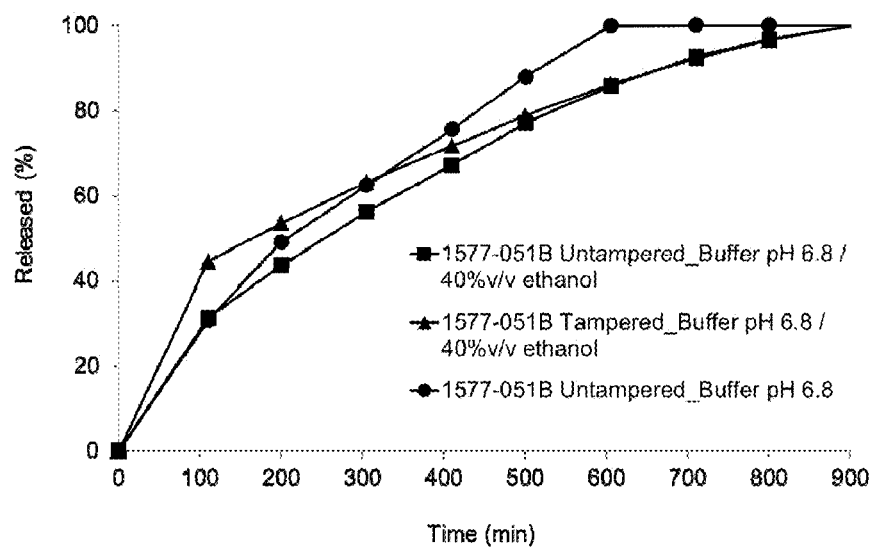
FIG. 6 shows in vitro dissolution results of the release of oxycodone (%) versus time (minutes) in phosphate buffer solution pH 6.8 with and without 40% v/v ethanol. The release of oxycodone is shown for intact tablets (untampered) and ground tablets (tampered) of one embodiment of a pharmaceutical composition, as disclosed herein, comprising PEO 600,000 daltons.

The composition was subjected to the dissolution test (controlled release) described above. The results are shown in FIG. 6 as the release of oxycodone (%) versus time (minutes) in phosphate buffer solution pH 6.8 with and without 40% v/v ethanol. The release of oxycodone is shown for intact tablets and ground tablets (ground in a Moulinex-1411R coffee grinder).

The viscosity of the composition was measured as described above. The viscosity was found to be 74 Pa·s at 5 rpm (using Viscosity Test #1).

Figure 7:
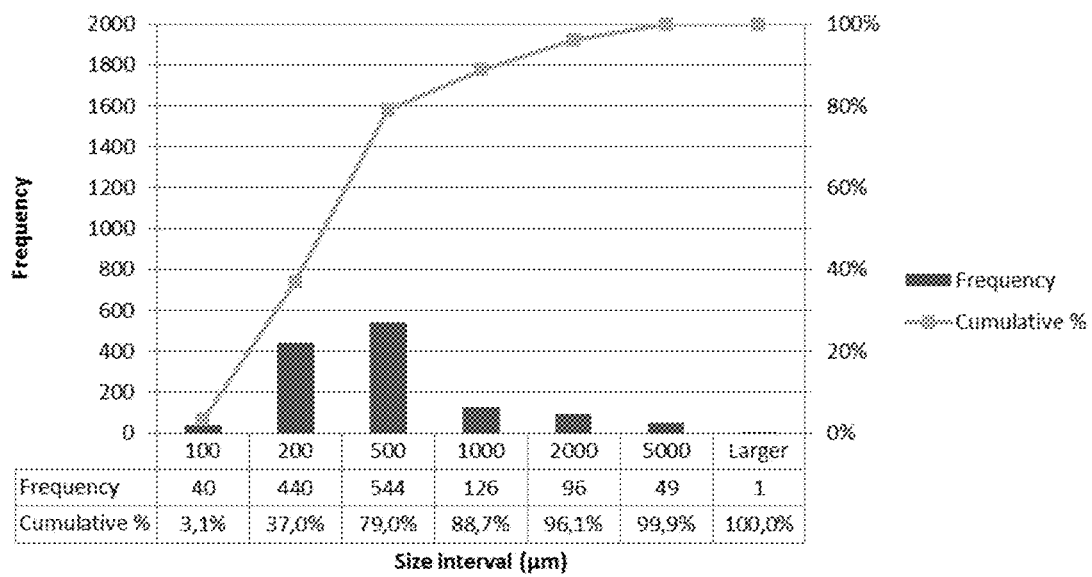
FIG. 7 shows particle size reduction results of one embodiment of a ground (tampered) pharmaceutical composition as disclosed herein comprising PEO 600,000 daltons.

Particle size reduction of the composition was measured as described above. The average particle size was 0.455±0.639 mm and the five largest particles were; 12.1 mm; 4.0 mm; 3.9 mm; 3.8 mm; and 3.7 mm. The results are shown in FIG. 7.

Example 3

Preparation of a Pharmaceutical Compositions Containing PEO 2,000,000 for Use According to the Disclosure A composition (batch No. 1581-065) according to the disclosure was prepared from the following ingredients:

| Composition | mg |
| --- | --- |
| PEO 2,000,000 | 188 |
| Poloxamer 188 | 50.2 |
| Hydromorphone HCl | 12.55 |

The composition was prepared as described above.

Figure 8:
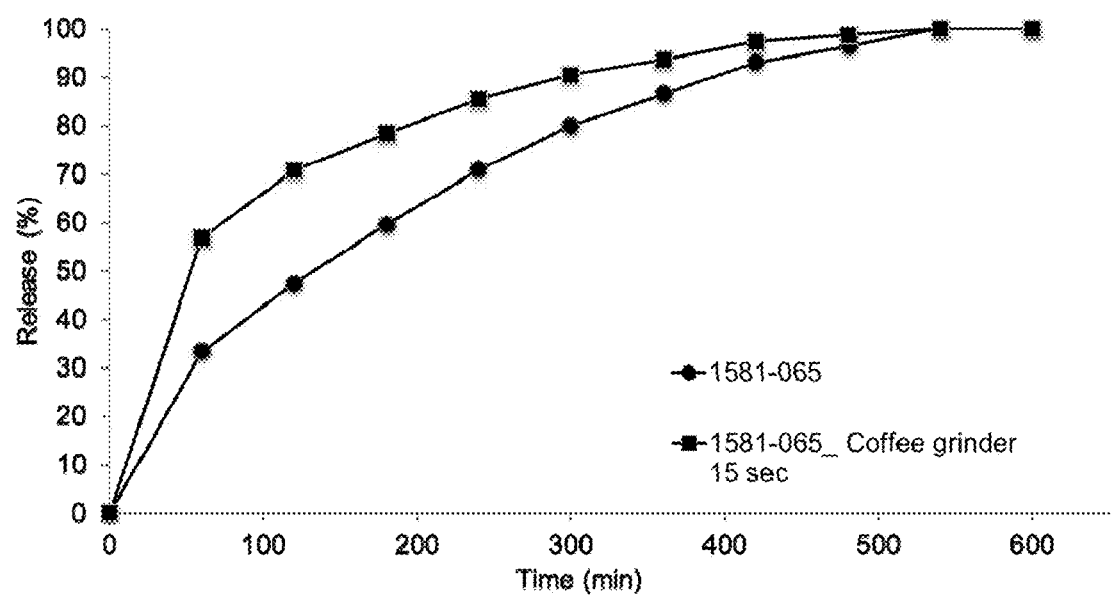
FIG. 8 shows in vitro dissolution results of the release of hydromorphone (%) versus time (minutes) in phosphate buffer solution pH 6.8. The release of hydromorphone is shown for intact tablets (untampered) and ground tablets (tampered) of one embodiment of a pharmaceutical composition, as disclosed herein, comprising PEO 2,000,000 daltons.

The composition was subjected to the dissolution test (controlled release) described above. The results are shown in FIG. 8 as the release of hydromorphone (%) versus time (minutes) in phosphate buffer solution pH 6.8 for intact tablets and ground tablets (ground in a Moulinex-1411R coffee grinder).

The viscosity of the compositions was measured as described above. The viscosity was found to be 46 Pa·s at 5 rpm (using Viscosity Test #1).

Figure 9:
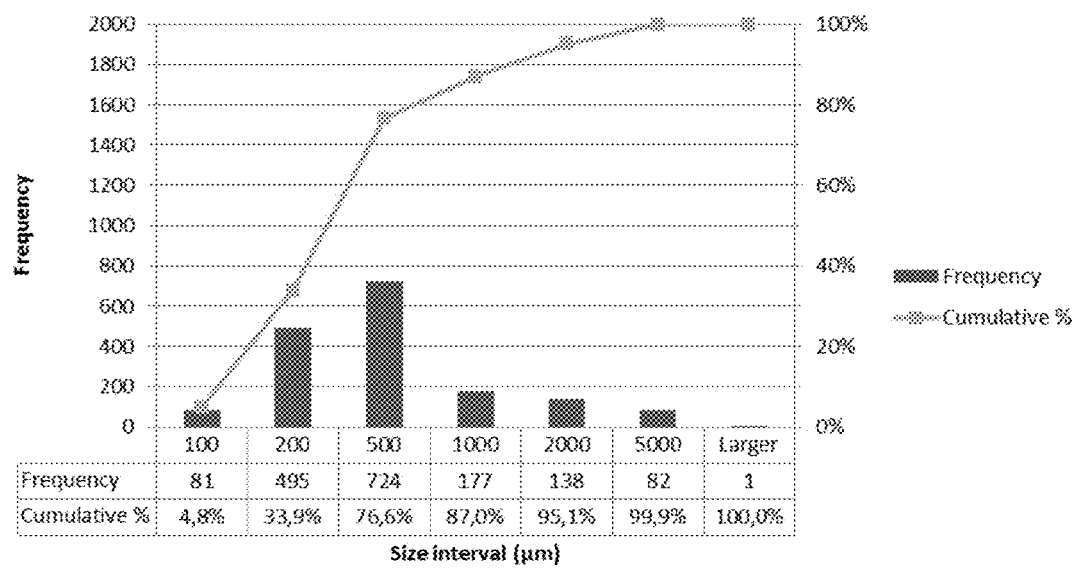
FIG. 9 shows particle size reduction results of one embodiment of a ground (tampered) pharmaceutical composition, as disclosed herein, comprising PEO 2,000,000 daltons.

Particle size reduction of the composition was measured as described above. The average particle size was 0.495±0.643 mm and the five largest particles were 10.5 mm; 3.6 mm; 3.6 mm; 3.5 mm; and 3.5 mm. The results are shown in FIG. 9.

Example 4

Preparation of a Pharmaceutical Composition Containing PEO 10,000,000 According to the Disclosure A composition (batch no. 1581-066) according to the disclosure was prepared from the following ingredients:

| Composition | mg |
| --- | --- |
| PEO 10,000,000 | 110 |
| Poloxamer 188 | 80 |
| Oxymorphone HCl | 10 |

The composition was prepared as described above.

Figure 10:
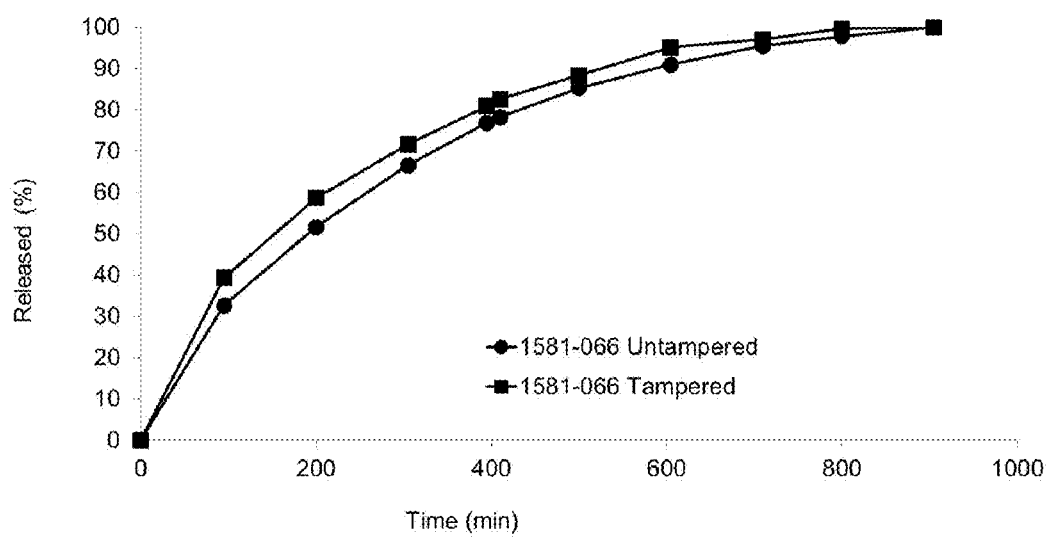
FIG. 10 shows in vitro dissolution results of the release of oxymorphone (%) versus time (minutes) in phosphate buffer solution pH 6.8. The release of oxymorphone is shown for intact tablets (untampered) and ground tablets (tampered) of one embodiment of a pharmaceutical composition as disclosed herein comprising PEO 10,000,000 daltons.

The composition was subjected to the dissolution test (controlled release) described above. The results are shown in FIG. 10 as the release of oxymorphone (%) versus time (minutes) in phosphate buffer solution pH 6.8 for intact tablets and ground tablets (ground in a Moulinex-1411R coffee grinder).

The viscosity of the composition was measured as described above. The viscosity was found to be 79.6 Pa·s at 5 rpm (using Viscosity Test #1).

Figure 11:
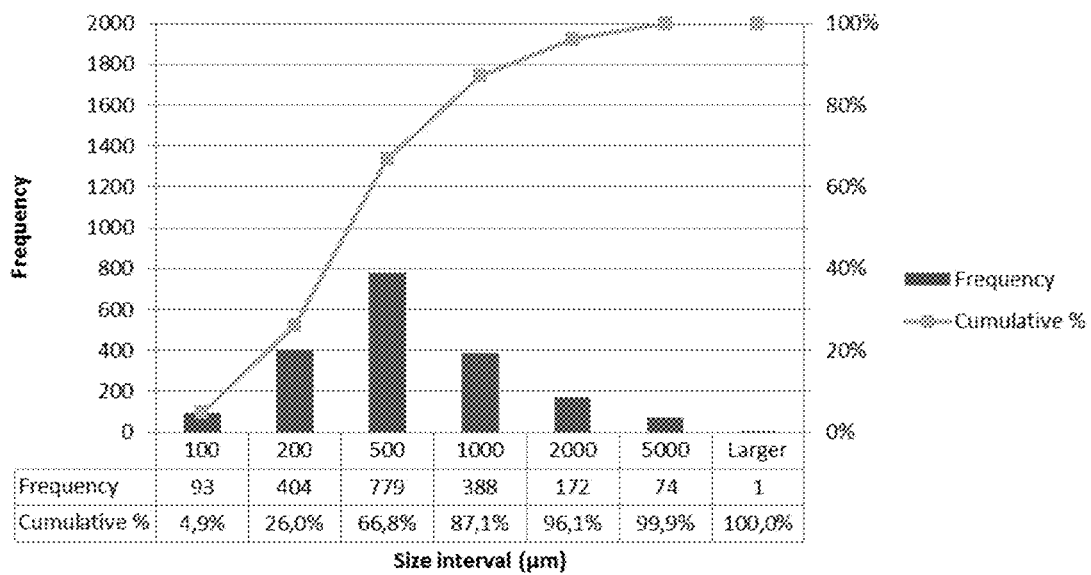
FIG. 11 shows particle size reduction results of one embodiment of a ground (tampered) pharmaceutical composition as disclosed herein comprising PEO 10,000,000 daltons.

Particle size reduction of the composition was measured as described above. The average particle size was 0.547±0.640 mm and the five largest particles were 5.8 mm; 4.8 mm; 4.7 mm; 4.7 mm; and 4.4 mm. The results are shown in FIG. 11.

Example 5

Oxycontin® OP 40 mg

Figure 12:
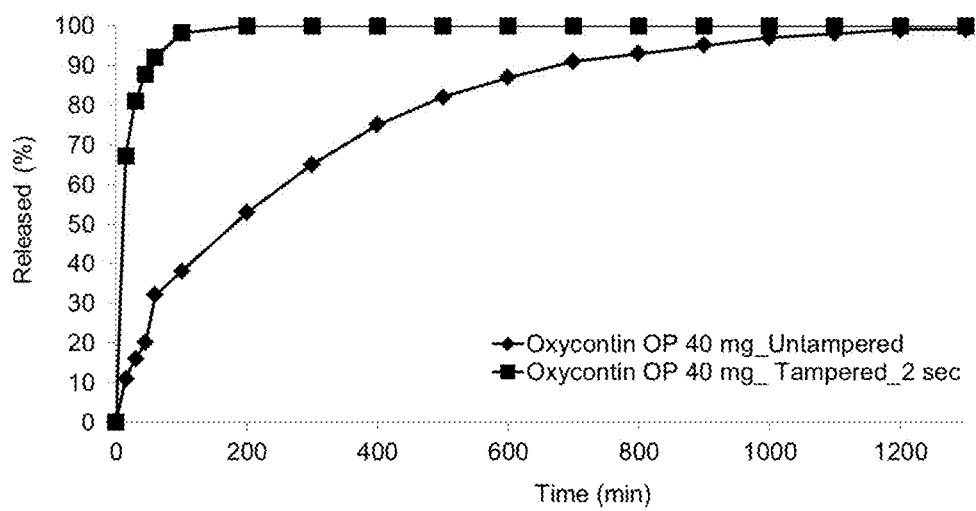
FIG. 12 shows in vitro dissolution results of the release of oxycodone (%) versus time (minutes) in phosphate buffer solution pH 6.8. The release of oxycodone is shown for intact tablets (untampered) and ground tablets (tampered) of Oxycontin® OP 40 mg.

Oxycontin® OP 40 mg was subjected to the dissolution test (controlled release) described above. The results are shown in FIG. 12 as the release of oxycodone (%) versus time (minutes) in phosphate buffer solution pH 6.8 for intact tablets and ground tablets (ground in a Moulinex-1411R coffee grinder).

The viscosity of Oxycontin® OP 40 mg was measured as described above. The viscosity was found to be 46 Pa·s at 5 rpm (using Viscosity Test #1).

Figure 13:
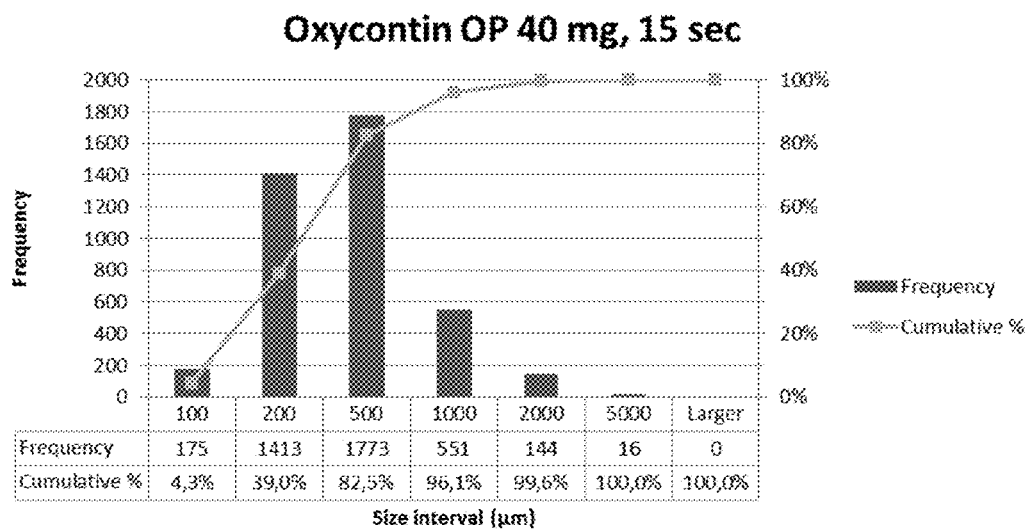
FIG. 13 shows particle size reduction results of a ground Oxycontin® OP 40 mg tablet.

Particle size reduction of Oxycontin® OP 40 mg was measured as described above. The average particle size was 0.341±0.301 mm and the five largest particles were 3.0 mm; 2.7 mm; 2.7 mm; 2.6 mm; and 2.4 mm. The results are shown in FIG. 13.

Example 6

Preparation of Morphine Prolonged Release Pharmaceutical Composition for Use According to the Disclosure A 200 mg morphine composition (batch No. 12-0060-067) according to the disclosure was prepared from the following ingredients:

| Composition | Mg |
| --- | --- |
| PEO 200 000 | 291.6 |
| PEO 600 000 | 291.6 |
| Morphine Sulphate Pentahydrate | 197.2 |
| BHT | 0.8 |

Figure 14:
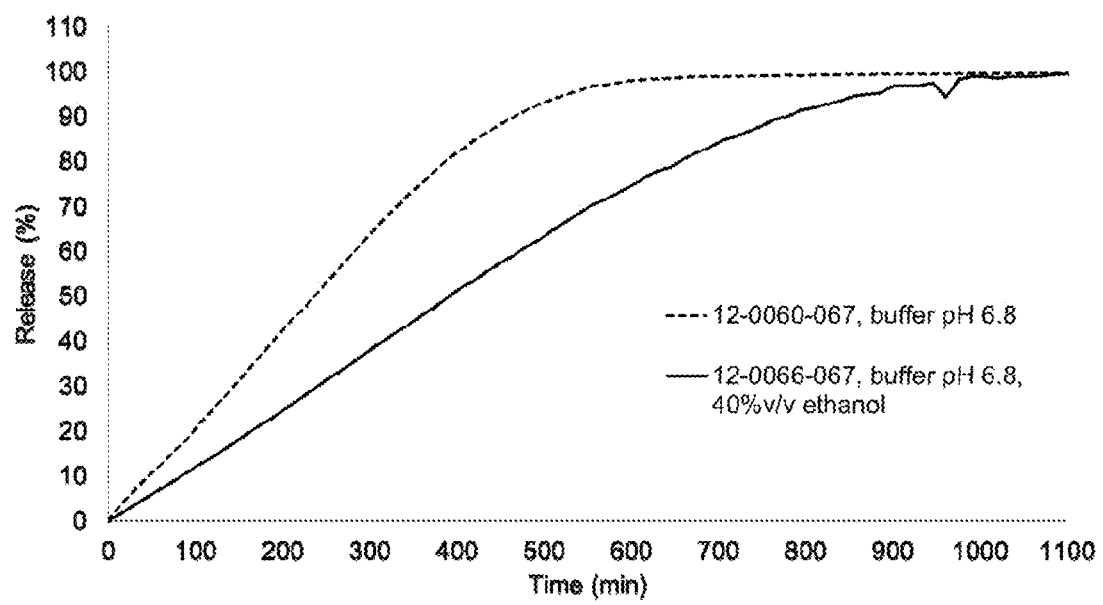
FIG. 14 shows in vitro dissolution results of the release of morphine (%) versus time (minutes) in phosphate buffer solution pH 6.8 with and without 40% v/v ethanol. The release of morphine is shown for intact tablets of one embodiment of a pharmaceutical composition, as disclosed herein.

The composition was subjected to the no alcohol-induced dose dumping test described above. The results are shown in FIG. 14 as release of morphine (%) versus time (minutes) in phosphate buffer solution pH 6.8 with/without 40% v/v ethanol. The release of morphine is shown for intact tablets.

Example 7

Crisping Test

A 60 mg morphine composition (batch No. 12-066-067) according to the disclosure was prepared from the following ingredients:

| Composition | Mg |
| --- | --- |
| PEO 200 000 | 354.3 |
| PEO 600 000 | 354.3 |
| Morphine Sulphate Pentahydrate | 60 |
| BHT | 0.8 |

The composition was subjected to the crisping test described above. For comparison, MST Continus® 60 mg, Oxycontin® OP 80 mg and Opana® ER 40 mg (containing hydroxypropyl methylcellulose (HPMC)) were subjected to the same crisping test.

The composition of MST Continus® and the composition of MS Contin® are identical. MST Continus® is the European trademark and MS Contin® is the American trademark.

The results are shown in Table 1 below.

TABLE 1

| Crisping (minutes) | | Morphine composition 60 mg | MST Continus ® 60 mg | Oxycontin ® OP 80 mg | Opana ® ER 40 mg |
|---|---|---|---|---|---|
| 0 | Viscosity (mPas) | >2400 | 75 | >2400 | >2400 |
|   | Injectable | No | Yes | No | No |
|   | Assay (%) | 100 | 98 | 99 | 98 |
| 8 | Viscosity (mPas) | >2400 | 93 | 60 | >2400 |
|   | Injectable | No | Yes | Yes | No |
|   | Assay (%) | 99 | 99 | 99 | 98 |
| 16 | Viscosity (mPas) | >2400 | 0 | 0 | 30 |
|   | Injectable | No | Yes | Yes | Yes |
|   | Assay (%) | 97 | 96 | 73 | 99 |

Example 8

Test of Particle Size Reduction of Pharmaceutical Compositions by Use of a Coffee Grinder A 200 mg morphine composition (batch No. 2654-056) according to the disclosure was prepared from the following ingredients:

| Composition | Mg |
|---|---|
| PEO 200 000 | 291.6 |
| PEO 600 000 | 291.6 |
| Morphine Sulphate Pentahydrate | 197.2 |
| BHT | 0.8 |

Figure 15:
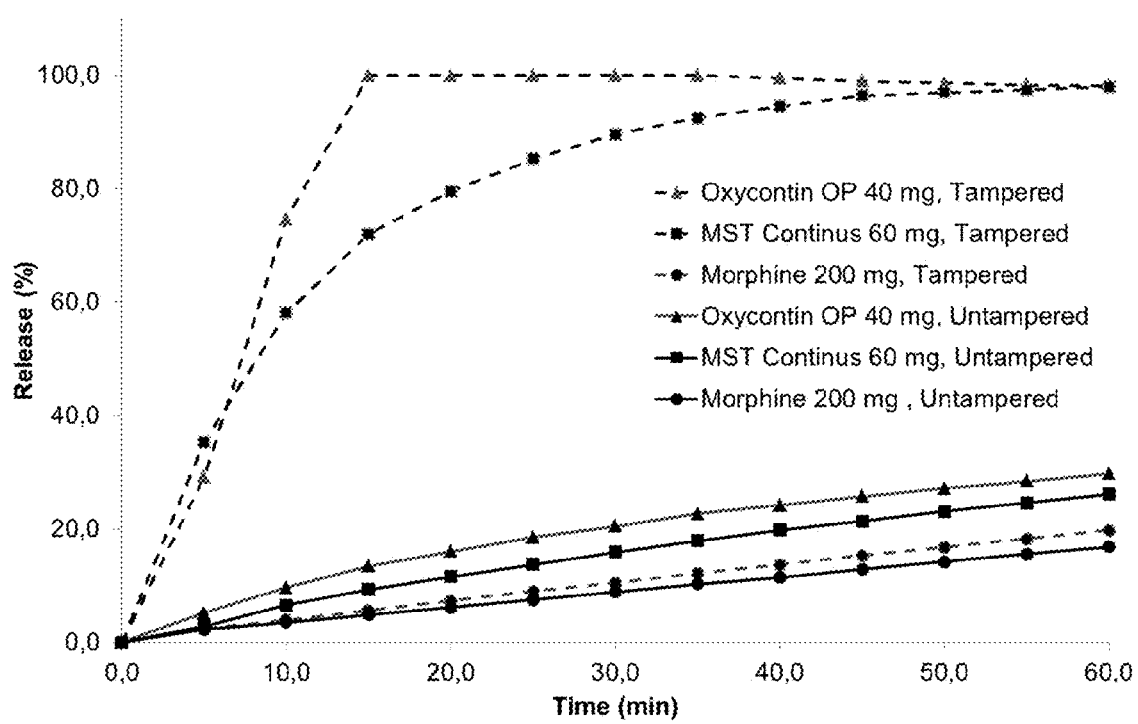
FIG. 15 shows in vitro dissolution results of release of active substance (%) versus time (minutes) in phosphate buffer solution pH 6.8. The release of active substance is shown for intact tablets and ground tablets (ground in a Krups F203 coffee grinder) of Oxycontin® OP 40 mg, MST Continus® 60 mg, and an embodiment of a pharmaceutical composition, as disclosed herein, containing 200 mg of morphine.

The composition was subjected to the dissolution test (controlled release) described above. The results are shown in FIG. 15 as the release of active substance (%) versus time (minutes) in phosphate buffer solution pH 6.8. The release of active substance is shown for intact tablets and ground tablets (ground in a Krups F203 coffee grinder). For comparison, MST Continus® 60 mg and Oxycontin® OP 40 mg were subjected to the same test. The results are shown in FIG. 15.

Example 9

Test of Particle Size Reduction of Pharmaceutical Compositions by Use of a Nutmeg Grater A 200 mg morphine composition (batch No. 2654-056) according to the disclosure was prepared from the following ingredients:

| Composition | Mg |
|---|---|
| PEO 200 000 | 291.6 |
| PEO 600 000 | 291.6 |
| Morphine Sulphate Pentahydrate | 197.2 |
| BHT | 0.8 |

Figure 16:
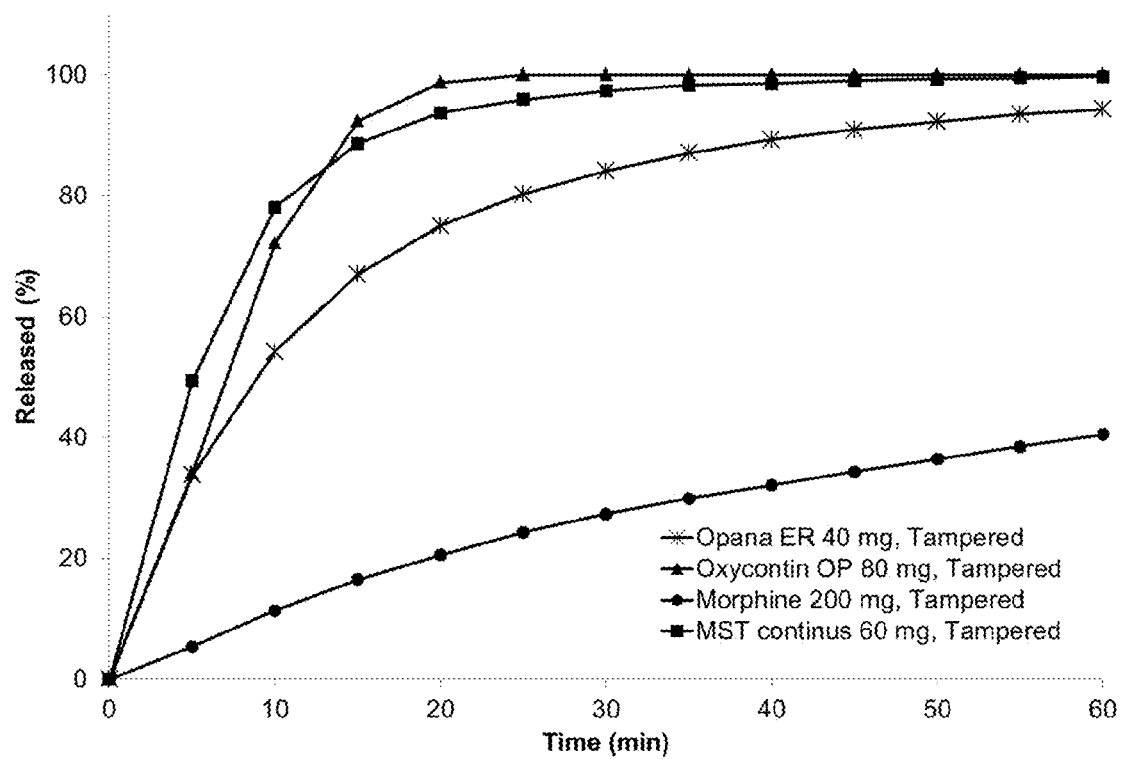
FIG. 16 shows in vitro dissolution results of release of active substance (%) versus time (minutes) in dilute hydrochloric acid. The release of active substance is shown for grated tablets (Nutmeg grater) of Opana® ER 40 mg, Oxycontin® OP 80 mg, MST Continus® 60 mg, and an embodiment of a pharmaceutical composition, as disclosed herein, containing 200 mg of morphine.

The composition was subjected to the dissolution test (immediate release) described above. The results are shown in FIG. 16 as the release of active substance (%) versus time (minutes) in dilute hydrochloric acid. The release of active substance is shown for grated tablets (Nutmeg grater). For comparison, MST Continus® 60 mg, Oxycontin® OP 80 mg and Opana® ER 40 mg were subjected to the same test. The results are shown in FIG. 16.

Figure 17:
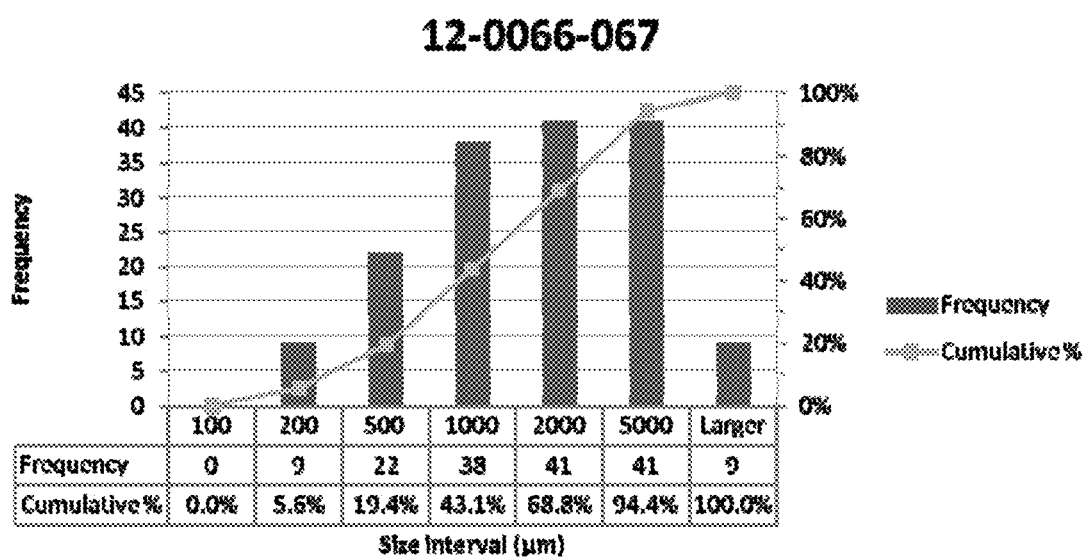
FIG. 17 shows particle size reduction results of a grated tablet of an embodiment of a pharmaceutical composition, as disclosed herein, containing 200 mg of morphine.

Particle size reduction of the composition was measured as described above. The average particle size was 1.94±2.57 mm and the five largest particles were 21.4 mm; 15.1 mm; 12.8 mm; 8.7 mm; and 7.8 mm. The results are shown in FIG. 17.

Figure 18:
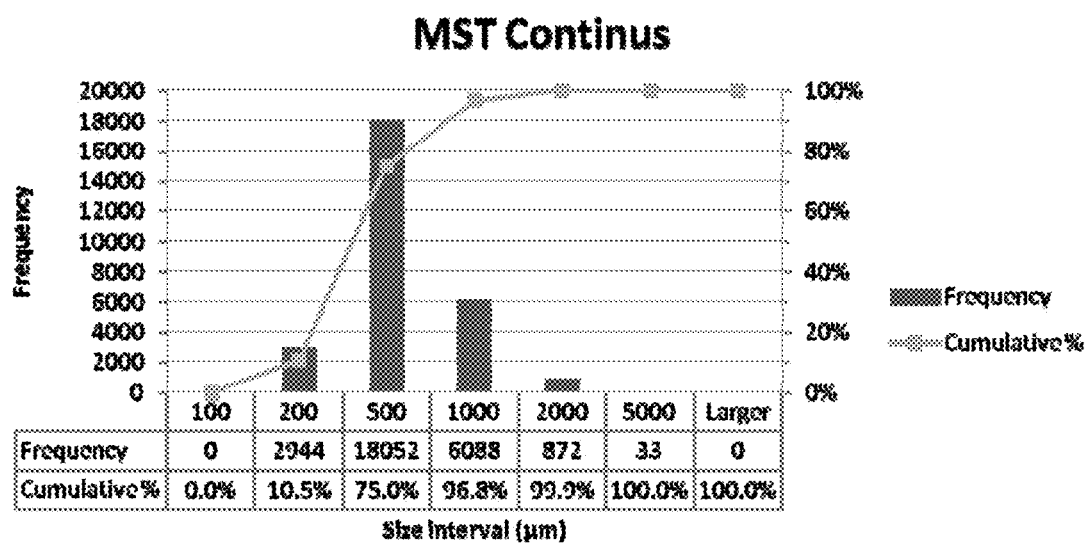
FIG. 18 shows particle size reduction results of a grated MST Continus® 60 mg tablet.
Figure 19:
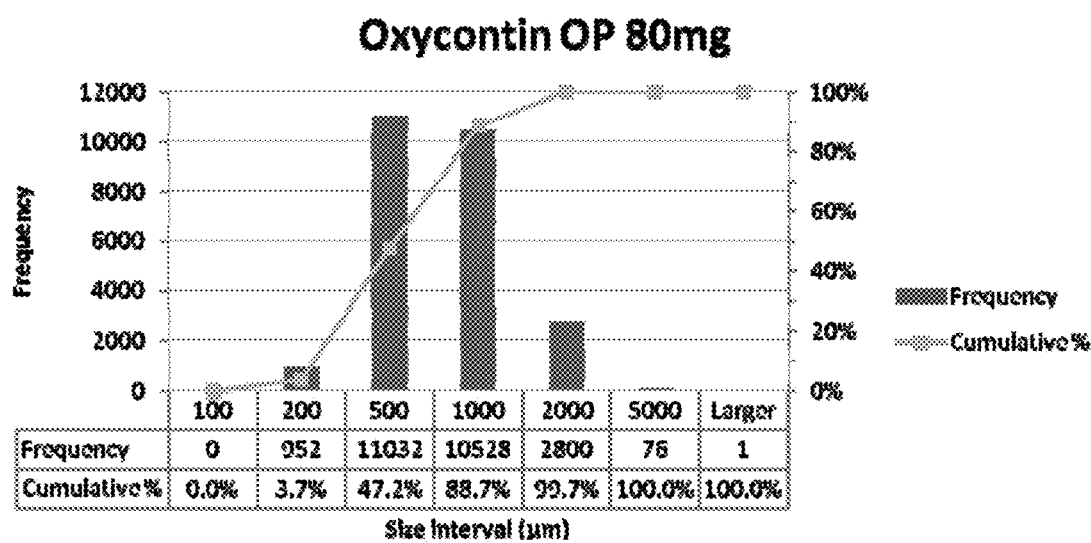
FIG. 19 shows particle size reduction results of a grated Opana® ER 40 mg tablet.
Figure 20:
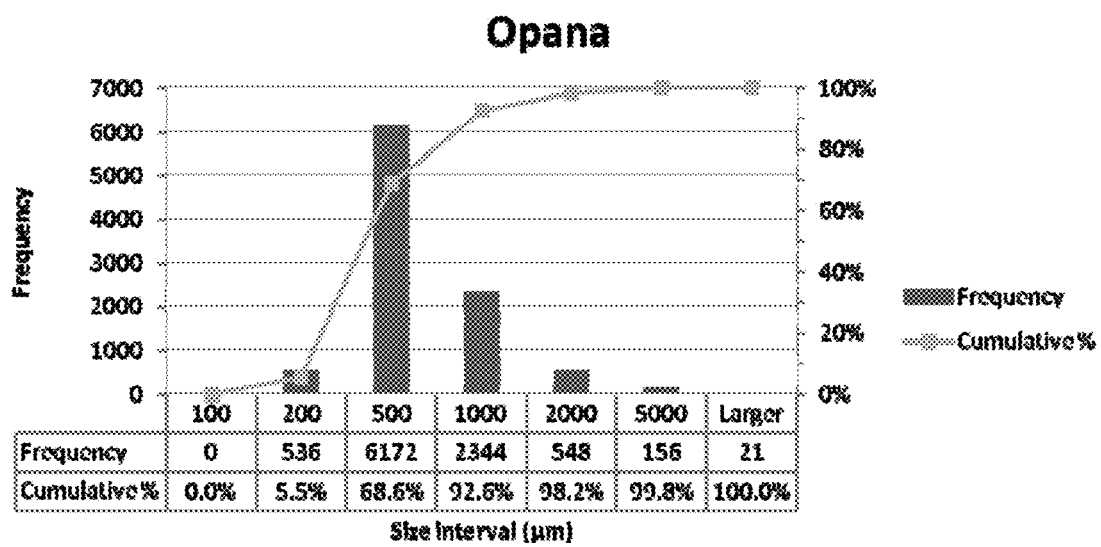
FIG. 20 shows particle size reduction results of a grated Oxycontin® OP 80 mg tablet.

For comparison, MST Continus® 60 mg, Oxycontin® OP 80 mg and Opana® ER 40 mg were subjected to the same test. For MST Continus® 60 mg, the average particle size was 0.410±0.250 mm and the five largest particles were 4.9 mm; 4.7 mm; 4.1 mm; 3.7 mm; and 3.5 mm. For Oxycontin® OP 80 mg, the average particle size was 0.596±0.337 mm and the five largest particles were 5.9 mm; 5.0 mm; 4.3 mm; 3.4 mm; and 3.1 mm. For Opana® ER 40 mg, the average particle size was 0.513±0.489 mm and the five largest particles were 9.4 mm; 8.7 mm; 7.8 mm; 6.8 mm; and 6.4 mm. The results are shown in FIGS. 18-20.

The five largest particles were lumps; some were big lumps and also big and flakey.

The dimensions of the tablets are shown in Table 2 below.

TABLE 2

| Tablet | Length, mm | Height, mm | Width, mm | Depth, mm (convex tablet) |
|---|---|---|---|---|
| Morphine composition 200 mg | 19.5 | 6.2 | 7.4 | N/A |
| MST Continus ® 60 mg | 7.25 | 4.5 | 7.25 | N/A |
| Oxycontin ® OP 80 mg | 9.5 | 4.25 | 9.5 | N/A |
| Opona ® ER 40 mg | 8.6 | 3.5 | 8.6 | 0.5 |

Example 10

Extraction Test

A 60 mg morphine composition (batch No. 12-066-067) according to the disclosure was prepared from the following ingredients:

| Composition | Mg |
|---|---|
| PEO 200 000 | 354.3 |
| PEO 600 000 | 354.3 |
| Morphine Sulphate Pentahydrate | 60 |
| BHT | 0.8 |

The composition was subjected to the extraction test described above. Two (2) tablets were placed in a 50 ml beaker, 10 ml solvent (purified water or Coca-Cola®) was added, and the beaker was sealed with Parafilm®. The beaker with tablets was left undisturbed at 25° C./60% RH for 24 hours. The free solvent was poured into a tared empty beaker, the viscosity of the free solvent was measured by the viscosity test as described above (Viscosity Test #2), and the active drug substance content in the free solvent (assay) was determined using HPLC with UV-detector.

By comparison, MST Continus® 60 mg, Oxycontin® OP 80 mg, and Opana® ER 40 mg were subjected to the same extraction test.

The results of are shown in table 3 below.

TABLE 3

| Formulation | Free solvent (ml) | Assay (%) | Viscosity (mPa s) | Injectable | Note |
|---|---|---|---|---|---|
| Morphine composition 60 mg | | | | | |
| Water | 5.8 | 30.8 | >2400 | No | Tablet shape disappeared |
| Coca-Cola ® | 3.2 | 24.4 | >2400 | No | Partly dissolved the rest having a white core |
| MST Continus ® 60 mg | | | | | |
| Water | 9.3 | 87.9 | 0 | Yes | Intact Spongy looking |
| Coca-Cola ® | 8.8 | 92.9 | 0 | Yes | Intact Spongy looking |
| Oxycontin ® OP 80 mg | | | | | |
| Water | 5.5 | 36.5 | 160 | Yes | Swollen transparent tablets |
| Coca-Cola ® | 5.5 | 48.4 | 68 | Yes | Swollen transparent tablets |
| Opana ® ER 40 mg | | | | | |
| Water | 5.0 | 50.1 | 73 | Yes | Swollen transparent tablets |
| Coca-Cola ® | 4.6 | 45.8 | 105 | Yes | Swollen transparent tablets |

The invention claimed is:

1. An abuse-deterrent tablet formulated for oral administration of an opioid, the tablet consisting of a tablet composition and, optionally, a cosmetic coat, wherein:
   the tablet composition comprises:
   about 1-30% w/w of the opioid; and
   about 70-98% w/w of a polyethylene oxide (PEO) having an average molecular weight of from about 400,000 daltons to about 600,000 daltons; and
   the cosmetic coat, when present, covers at least a portion of the tablet composition, and dissolves within 30 minutes after contact with an aqueous media,
   wherein the tablet composition does not provide immediate release of the opioid even after the abuse-deterrent tablet is subjected to physical tampering selected from crushing, grinding, grating, cutting, or crisping, and
   wherein the tablet composition exhibits a viscosity of at least 170 mPa·s when measured by Viscosity Test #2, or a viscosity of at least 46 Pa·s when measured by Viscosity Test #1.

2. The abuse deterrent tablet of claim 1, wherein the opioid is selected from the group consisting of buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol, dihydromorphine, and pharmaceutically acceptable salts thereof.

3. The abuse deterrent tablet of claim 1, wherein the opioid is selected from the group consisting of morphine and pharmaceutically acceptable salts thereof.

4. The abuse deterrent tablet of claim 1, wherein the tablet composition exhibits a release rate of opioid in ethanol that is equal to or lower than the release rate of opioid in water.

5. The abuse deterrent tablet of claim 1, wherein the tablet yields a non-snortable composition when subjected to physical tampering selected from crushing, hammering, grinding, grating, and cutting.

6. An abuse-deterrent tablet formulated for oral administration of an opioid, consisting of a tablet composition and, optionally, a cosmetic coat, wherein:
   the tablet composition comprises:
   about 1-30% w/w of the opioid; and
   about 70-98% w/w of a polyethylene oxide (PEO) blend comprising two or more PEOs, wherein each of the two or more PEOs has a different average molecular weight and the average molecular weight of the blend of the two or more PEOs included in the tablet composition is from about 400,000 daltons to about 600,000 daltons; and
   the cosmetic coat, when present, covers at least a portion of the tablet composition, and dissolves within 30 minutes after contact with an aqueous media,
   wherein the tablet composition does not provide immediate release of the opioid even after the abuse-deterrent tablet is subjected to physical tampering selected from crushing, grinding, grating, cutting, or crisping, and
   wherein the tablet composition exhibits a viscosity of at least 170 mPa·s when measured by Viscosity Test #2, or a viscosity of at least 46 Pa·s when measured by Viscosity Test #1.

7. The abuse deterrent tablet of claim 6, wherein the opioid is selected from the group consisting of buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol, dihydromorphine, and pharmaceutically acceptable salts thereof.

8. The abuse deterrent tablet of claim 6, wherein the opioid is selected from the group consisting of morphine and pharmaceutically acceptable salts thereof.

9. The abuse deterrent tablet of claim 6, wherein the PEO blend includes a first PEO having an average molecular weight of about 200,000 daltons and a second PEO having an average molecular weight of about 600,000 daltons, wherein the average molecular weight of the PEO blend included in the tablet composition is about 400,000 daltons.

10. The abuse deterrent tablet of claim 6, wherein the tablet composition exhibits a release rate of opioid in ethanol that is equal to or lower than the release rate of opioid in water.

11. The abuse deterrent tablet of claim 6, wherein the tablet yields a non-snortable composition when subjected to physical tampering selected from crushing, hammering, grinding, grating, and cutting.

12. An abuse-deterrent tablet formulated for oral administration of an opioid, consisting of a tablet composition and, optionally, a cosmetic coat, wherein:
   the tablet composition comprises:
   about 1-30% w/w of the opioid;
   about 70-98% w/w of a polyethylene oxide (PEO) selected from a single PEO having an average molecular weight of from about 400,000 daltons to about 600,000 daltons and a PEO blend comprising two or more PEOs, wherein each of the two or more PEOs has a different average molecular weight and the average molecular weight of the blend of the two or more PEOs included in the tablet composition is from about 400,000 daltons to about 600,000 daltons; and
   at least 1% w/w of a plasticizer; and
   the cosmetic coat, when present, covers at least a portion of the tablet composition, and dissolves within 30 minutes after contact with an aqueous media,
   wherein the tablet composition does not provide immediate release of the opioid even after the abuse-deterrent tablet is subjected to physical tampering selected from crushing, grinding, grating, cutting, or crisping, and wherein the tablet composition exhibits a viscosity of at least 170 mPa·s when measured by Viscosity Test #2 or a viscosity of at least 46 Pa·s when measured by Viscosity Test #1.

13. The abuse deterrent tablet of claim 12, wherein the opioid is selected from the group consisting of buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol, dihydromorphine, and pharmaceutically acceptable salts thereof.

14. The abuse deterrent tablet of claim 12, wherein the opioid is selected from the group consisting of morphine and pharmaceutically acceptable salts thereof.

15. The abuse deterrent tablet of claim 12, wherein the tablet composition exhibits a release rate of opioid in ethanol that is equal to or lower than the release rate of opioid in water.

16. The abuse deterrent tablet of claim 12, wherein the plasticizer is selected from the group consisting of poloxamers having an average molecular weight from about 3,000 to about 30,000 daltons.

17. The abuse deterrent tablet of claim 12, wherein the tablet yields a non-snortable composition when subjected to physical tampering selected from crushing, hammering, grinding, grating, and cutting.

18. A method for treating an individual suffering from moderate to severe pain, the method comprising administering to the individual an abuse-deterrent tablet according to claim 12.

19. A method for treating an individual suffering from moderate to severe pain, the method comprising administering to the individual an abuse-deterrent tablet according to claim 1.

20. A method for treating an individual suffering from moderate to severe pain, the method comprising administering to the individual an abuse-deterrent tablet according to claim 6.

21. The abuse deterrent tablet of claim 1, wherein the average molecular weight of the PEO included in the tablet composition is about 400,000 daltons.

22. The abuse deterrent tablet of claim 6, wherein the average molecular weight of the PEO blend included in the tablet composition is about 400,000 daltons.

23. The abuse deterrent tablet of claim 12, wherein the average molecular weight of the PEO or PEO blend included in the tablet composition is about 400,000 daltons.

* * * * *